(12) United States Patent
Reyes et al.

(10) Patent No.: US 9,895,431 B1
(45) Date of Patent: Feb. 20, 2018

(54) SIMIAN ADENOVIRAL VECTORS ENCODING MALARIA ANTIGEN

(75) Inventors: Arturo Reyes, Oxfordshire (GB);
Adrian Hill, Oxfordshire (GB);
Geraldine O'Hara, Oxfordshire (GB);
Stefano Colloca, Rome (IT); Riccardo Cortese, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 1218 days.

(21) Appl. No.: 12/595,576

(22) PCT Filed: Apr. 10, 2008

(86) PCT No.: PCT/GB2008/001175
§ 371 (c)(1),
(2), (4) Date: Feb. 16, 2010

(87) PCT Pub. No.: WO2008/122769
PCT Pub. Date: Oct. 16, 2008

(30) Foreign Application Priority Data

Apr. 10, 2007 (GB) .................................. 0706914.9
Sep. 13, 2007 (GB) .................................. 0717888.2

(51) Int. Cl.
| | | |
|---|---|---|
| A61K 39/00 | (2006.01) | |
| A61K 39/015 | (2006.01) | |
| A61P 35/00 | (2006.01) | |
| A61P 33/06 | (2006.01) | |
| C12N 15/861 | (2006.01) | |
| A61P 37/04 | (2006.01) | |
| C12N 15/86 | (2006.01) | |

(52) U.S. Cl.
CPC ............ *A61K 39/015* (2013.01); *C12N 15/86* (2013.01)

(58) Field of Classification Search
None
See application file for complete search history.

(56) References Cited

FOREIGN PATENT DOCUMENTS

| | | |
|---|---|---|
| EP | 1589108 A | 10/2005 |
| JP | 2002-506346 | 2/2002 |
| JP | 2003-509470 | 3/2003 |
| WO | 2005/071093 | 8/2005 |
| WO | 2007/027860 | 3/2007 |

OTHER PUBLICATIONS

Ellis (Vaccines, W.B. Saunders Company, Chapter 29, 1988.*
Boslego et al (Vaccines and Immunotherapy, 1991, Chapter 17).*
Skolnick et al. (Trends in Biotechnology 18: 34-39, 2000).*
Craig et al. (PLoS Pathogens vol. 8, No. 2.).*
Goodman et al. (Scientific Reports vol. 3, pp. 1-13).*
Reyes-Sandoval, Arturo, et al. "Single dose immunogenicity and protective efficacy of simian adenoviral vectors against plasmodium berghei" European Journal of Immunology; vol. 38, No. 3; Mar. 1, 2008; 732-741.
Martin, Rowena E., et al. "New vectored vaccines for malaria" MAM 2008 Oral Abstracts, International Journal of Parasitology; vol. 38; Dec. 22, 2007; S17-S33; Abstract 54.
Li, Shengqiang, et al. "Viral vectors for malaria vaccine development" Vaccine; vol. 25, No. 14; Mar. 15, 2007; 2567-2574.
McConkey, Samuel J., et al. "Enhanced T-cell immunogenicity of plasmid DNA vaccines boosted by recombinant modified vaccinia virus ankara in humans" Nature Medicine; vol. 9, No. 6; Jun. 1, 2003; 729-735.
Schneider, Joerg, et al. "A prime boost immunisation regimen using DNA followed by recombinant modified vaccinia virus Ankara induces strong cellular immune responses against the Plasmodium falciparum TRAP antigen in chimpanzees" Vaccine; vol. 19, No. 32; Sep. 14, 2001; 4595-4602.
Gilbert, Sarah C., et al. "Enhanced CD8 T Cell immunogenicity and protective efficacy in a mouse malaria model using a recombinant adenoviral vaccine in heterologous prime-boost immunisation regimes" Vaccine; vol. 20, No. 7-8; Jan. 15, 2002; 1039-1045.
Gilbert, Sarah C., et al "A protein particle vaccine containing multiple malaria epitopes" Nature Biotechnology; vol. 15; Nov. 1, 1997; 1280-1284.
Hill, Adrian V.S. "Pre-erythrocytic malaria vaccines: towards greater efficacy" Nature Reviews Immunology; vol. 6, No. 1; Jan. 2006; 21-32.
Moorthy, V.S., et al. "Safety of DNA and modified vaccinia virus Ankara vaccines against liver-stage P. falciparum malaria in non-immune volunteers" Vaccine; vol. 21, 2003; 1995-2002.
Robson, Kathryn.J.H. et al. "A highly conserved amino-acid sequence in thrombospondin, properdin and in proteins from sporozoites and blood stages of a human malaria parasite" Nature; vol. 335, No. 6185; Sep. 1, 1988; 79-82.
Rodrigues, Elaine G., et al. "Single immunizing dose of recombinant adenovirus efficiently induces CD8+ T cell-mediated protective immunity aganist malaria" Journal of Immunology; vol. 158, No. 3; Feb. 1, 1997; 1268-1274.
Aidoo, M., et al. "Identification of conserved antigenic components for a cytotoxic T lymphocyte-inducing vaccine against malaria" The Lancet; vol. 345, No. 8956; Apr. 22, 1995; 1003-1007.
Flanagan, Katie L., et al. "Cellular reactivity to the P. Falciparum protein trap in adult kenyans: novel epitopes, complex cytokine patterns, and the impact of natural antigenic variation" American Journal of Tropical Medicine & Hygiene; vol. 74, No. 3; Mar. 1, 2006; 367-375.

(Continued)

*Primary Examiner* — Robert A Zeman
(74) *Attorney, Agent, or Firm* — Virginia G. Campen

(57) ABSTRACT

The invention provides recombinant adenoviral vectors which are capable of eliciting immunity against the pre-erythrocytic stage of the life cycle of the malaria parasite. In particular, the invention provides a recombinant, replication deficient simian adenoviral vector which encodes an antigen comprising the thrombospondin-related adhesion protein (TRAP), and also immunogenic compositions (e.g. vaccines) comprising the vector and methods of using such compositions.

7 Claims, 12 Drawing Sheets

(56) References Cited

OTHER PUBLICATIONS

Xiang, Z., et al. "Novel, chimpanzee serotype 68-based adenoviral vaccine carrier for induction of antibodies to a transgene product." J Virol. Mar. 2002;76(6):2667-75.

Xiang, Z., et al. "Novel, Chimpanzee Serotype 68-Based Adenoviral Vaccine Carrier for Induction of Antibodies to a Transgene Product." Journal of Virology. Mar. 2002;76(6):2667-2675.

* cited by examiner

SEQUENCE LISTING

```
<160> NUMBER OF SEQ ID NOS: 2

<210> SEQ ID NO 1
<211> LENGTH: 2402
<212> TYPE: DNA
<213> ORGANISM: Artificial Sequence
<220> FEATURE:
<223> OTHER INFORMATION: Vector insert encoding ME.TRAP antigen

<400> SEQUENCE: 1
gatcccgccg ccaccatggg tatgatcaac gcctacttgg acaagttgat ctccaagtac      60
gaagacgaaa tctcctacat cccatctgcc gaaaagatcg gatctaagcc gaacgacaag     120
tccttgtata aacctaagga cgaattggac tacaagccaa tcgttcaata cgacaacttc     180
ggatctgcct ccaagaacaa ggaaaaggct ttgatcatcg gtatcgctgg tggtttggcc     240
ttgttgatga accctaatga cccaaacaga acgtcagat ctcacttggg taacgttaag      300
tacttggtta agtctttgta cgatgaacac atcttattga tggactgttc tggttctatt     360
ggatctgacc caaacgctaa cccaaacgtt gacccaaacg ccaacccaaa cgtccaagtt     420
cacttccaac cattgcctcc ggccgttgtc aagttgcaat tcatcaaggc caactctaag     480
ttcatcggta tcaccgaagg atcttacttg aacaaaattc aaaactcttt gatggaaaag     540
ttgaaagaat tggaaaaggc tacttctgtc ttggctggtt tgggatctaa cgctaatcca     600
aacgcaaatc cgaacgccaa tcctaacgcg aatcccgacg aatggtctcc atgttctgtc     660
acttgtggta agggtactcg ctctagaaag agagaaggat ccaaaataat gaatcatctt     720
gggaatgtta aatatttagt cattgtgttt ttgattttct ttgatttgtt tctagttaat     780
ggtagagatg tgcaaaacaa tatagtggat gaaataaaat atagtgaaga agtatgtaat     840
gatcaggtag atctttacct tctaatggat tgttctggaa gtatacgtcg tcataattgg     900
gtgaaccatg cagtacctct agctatgaaa ttgatacaac aattaaatct taatgataat     960
gcaattcact tatatgttaa tgtttttttca aacaatgcaa agaaattat tagattacat    1020 agtgatgcat ctaaaaacaa agagaaggct ttaattatta taggtcact cttaagtaca    1080 aatcttccat atggtagaac aaacttaact gatgcactgt tacaagtaag aaaacattta    1140
aatgaccgaa tcaatagaga gaatgctaat caattagttg ttatattaac agatggaatt    1200
ccagatagta ttcaagattc attaaaagaa tcaagaaaat taagtgatcg tggtgttaaa    1260
atagctgttt ttggtattgg acaaggtatt aatgtagctt tcaacagatt tcttgtaggt    1320
tgtcatccat cagatggtaa atgtaacttg tatgctgatt ctgcatggga aaatgtaaaa    1380
aatgttatcg gacccttttat gaaggctgtt tgtgttgaag tagaaaaaac agcaagttgt    1440
ggtgtttggg acgaatggtc tccatgtagt gtaacttgtg gtaaaggtac caggtcaaga    1500
aaaagagaaa tcttacacga aggatgtaca agtgaaatac aagaacaatg tgaagaagaa    1560
agatgtcctc caaaatggga accattagat gttccagatg aacccgaaga tgatcaacct    1620
agaccaagag gagataattc ttctgtccaa aaaccagaag aaaatataat agataataat    1680
ccacaagaac cttcaccaaa tccagaagaa ggaaaggatg aaaatccaaa cggatttgat    1740
```

```
ttagatgaaa atccagaaaa tccaccaaat ccagatattc ctgaacaaaa addaaatata   1800
cctgaagatt cagaaaaaga agtaccttct gatgttccaa aaaatccaga agacgatcga   1860
gaagaaaact ttgatattcc aaagaaaccc gaaaataagc acgataatca aaataattta   1920
ccaaatgata aaagtgatag aaatattcca tattcaccat tacctccaaa agttttggat   1980
aatgaaagga acaaagtga cccccaaagt caagataata atggaaatag gcacgtacct   2040
aatagtgaag atagagaaac acgtccacat ggtagaaata atgaaaatag atcatacaat   2100
agaaaatata acgatactcc aaaacatcct gaaagggaag aacatgaaaa gccagataat   2160
aataaaaaaa aaggagaatc agataataaa tataaaattg caggtggaat agctggagga   2220
ttagctttac tcgcatgtgc tggacttgct tataaattcg tagtaccagg agcagcaaca   2280
ccctatgccg gagaacctgc acctttgat gaaacattag gtgaagaaga taaagatttg   2340
gacgaacctg aacaattcag attacctgaa gaaaacgagt ggaattaaat ataatacgga   2400
tc                                                                 2402
```

<210> SEQ ID NO 2
<211> LENGTH: 790
<212> TYPE: PRT
<213> ORGANISM: Artificial Sequence
<220> FEATURE:
<223> OTHER INFORMATION: ME.TRAP antigen

<400> SEQUENCE: 2

```
Met Gly Met Ile Asn Ala Tyr Leu Asp Lys Leu Ile Ser Lys Tyr Glu
1               5                   10                  15

Asp Glu Ile Ser Tyr Ile Pro Ser Ala Glu Lys Ile Gly Ser Lys Pro
                20                  25                  30

Asn Asp Lys Ser Leu Tyr Lys Pro Lys Asp Glu Leu Asp Tyr Lys Pro
            35                  40                  45

Ile Val Gln Tyr Asp Asn Phe Gly Ser Ala Ser Lys Asn Lys Glu Lys
        50                  55                  60

Ala Leu Ile Ile Gly Ile Ala Gly Gly Leu Ala Leu Leu Met Asn Pro
65                  70                  75                  80

Asn Asp Pro Asn Arg Asn Val Arg Ser His Leu Gly Asn Val Lys Tyr
                85                  90                  95

Leu Val Lys Ser Leu Tyr Asp Glu His Ile Leu Leu Met Asp Cys Ser
                100                 105                 110

Gly Ser Ile Gly Ser Asp Pro Asn Ala Asn Pro Asn Val Asp Pro Asn
            115                 120                 125

Ala Asn Pro Asn Val Gln Val His Phe Gln Pro Leu Pro Pro Ala Val
        130                 135                 140

Val Lys Leu Gln Phe Ile Lys Ala Asn Ser Lys Phe Ile Gly Ile Thr
145                 150                 155                 160

Glu Gly Ser Tyr Leu Asn Lys Ile Gln Asn Ser Leu Met Glu Lys Leu
                165                 170                 175

Lys Glu Leu Glu Lys Ala Thr Ser Val Leu Ala Gly Leu Gly Ser Asn
            180                 185                 190

Ala Asn Pro Asn Ala Asn Pro Asn Ala Asn Pro Asn Ala Asn Pro Asp
        195                 200                 205

Glu Trp Ser Pro Cys Ser Val Thr Cys Gly Lys Gly Thr Arg Ser Arg
    210                 215                 220

Lys Arg Glu Gly Ser Lys Ile Met Asn His Leu Gly Asn Val Lys Tyr
225                 230                 235                 240
```

```
Leu Val Ile Val Phe Leu Ile Phe Phe Asp Leu Phe Leu Val Asn Gly
            245                 250                 255

Arg Asp Val Gln Asn Asn Ile Val Asp Glu Ile Lys Tyr Ser Glu Glu
        260                 265                 270

Val Cys Asn Asp Gln Val Asp Leu Tyr Leu Leu Met Asp Cys Ser Gly
        275                 280                 285

Ser Ile Arg Arg His Asn Trp Val Asn His Ala Val Pro Leu Ala Met
        290                 295                 300

Lys Leu Ile Gln Gln Leu Asn Leu Asn Asp Asn Ala Ile His Leu Tyr
305                 310                 315                 320

Val Asn Val Phe Ser Asn Asn Ala Lys Glu Ile Ile Arg Leu His Ser
                325                 330                 335

Asp Ala Ser Lys Asn Lys Glu Lys Ala Leu Ile Ile Ile Arg Ser Leu
                340                 345                 350

Leu Ser Thr Asn Leu Pro Tyr Gly Arg Thr Asn Leu Thr Asp Ala Leu
            355                 360                 365

Leu Gln Val Arg Lys His Leu Asn Asp Arg Ile Asn Arg Glu Asn Ala
        370                 375                 380

Asn Gln Leu Val Val Ile Leu Thr Asp Gly Ile Pro Asp Ser Ile Gln
385                 390                 395                 400

Asp Ser Leu Lys Glu Ser Arg Lys Leu Ser Asp Arg Gly Val Lys Ile
                405                 410                 415

Ala Val Phe Gly Ile Gly Gln Gly Ile Asn Val Ala Phe Asn Arg Phe
                420                 425                 430

Leu Val Gly Cys His Pro Ser Asp Gly Lys Cys Asn Leu Tyr Ala Asp
            435                 440                 445

Ser Ala Trp Glu Asn Val Lys Asn Val Ile Gly Pro Phe Met Lys Ala
450                 455                 460

Val Cys Val Glu Val Glu Lys Thr Ala Ser Cys Gly Val Trp Asp Glu
465                 470                 475                 480

Trp Ser Pro Cys Ser Val Thr Cys Gly Lys Gly Thr Arg Ser Arg Lys
                485                 490                 495

Arg Glu Ile Leu His Glu Gly Cys Thr Ser Glu Ile Gln Glu Gln Cys
                500                 505                 510

Glu Glu Glu Arg Cys Pro Pro Lys Trp Glu Pro Leu Asp Val Pro Asp
            515                 520                 525

Glu Pro Glu Asp Asp Gln Pro Arg Pro Arg Gly Asp Asn Ser Ser Val
            530                 535                 540

Gln Lys Pro Glu Glu Asn Ile Ile Asp Asn Asn Pro Gln Glu Pro Ser
545                 550                 555                 560

Pro Asn Pro Glu Glu Gly Lys Asp Glu Asn Pro Asn Gly Phe Asp Leu
                565                 570                 575

Asp Glu Asn Pro Glu Asn Pro Asn Pro Asp Ile Pro Glu Gln Lys
            580                 585                 590

Pro Asn Ile Pro Glu Asp Ser Glu Lys Glu Val Pro Ser Asp Val Pro
            595                 600                 605

Lys Asn Pro Glu Asp Asp Arg Glu Glu Asn Phe Asp Ile Pro Lys Lys
        610                 615                 620

Pro Glu Asn Lys His Asp Asn Gln Asn Asn Leu Pro Asn Asp Lys Ser
625                 630                 635                 640

Asp Arg Asn Ile Pro Tyr Ser Pro Leu Pro Pro Lys Val Leu Asp Asn
                645                 650                 655

Glu Arg Lys Gln Ser Asp Pro Gln Ser Gln Asp Asn Asn Gly Asn Arg
```

-continued

```
                660                 665                 670
His Val Pro Asn Ser Glu Asp Arg Glu Thr Arg Pro His Gly Arg Asn
        675                 680                 685

Asn Glu Asn Arg Ser Tyr Asn Arg Lys Tyr Asn Asp Thr Pro Lys His
        690                 695                 700

Pro Glu Arg Glu Glu His Glu Lys Pro Asp Asn Asn Lys Lys Lys Gly
705                     710                 715                 720

Glu Ser Asp Asn Lys Tyr Lys Ile Ala Gly Gly Ile Ala Gly Gly Leu
                725                 730                 735

Ala Leu Leu Ala Cys Ala Gly Leu Ala Tyr Lys Phe Val Val Pro Gly
            740                 745                 750

Ala Ala Thr Pro Tyr Ala Gly Glu Pro Ala Pro Phe Asp Glu Thr Leu
        755                 760                 765

Gly Glu Glu Asp Lys Asp Leu Asp Glu Pro Glu Gln Phe Arg Leu Pro
        770                 775                 780

Glu Glu Asn Glu Trp Asn
785                 790
```

SIMIAN ADENOVIRAL VECTORS ENCODING MALARIA ANTIGEN

The present application is §371 application of PCT/GB2008/001175 filed Apr. 10, 2008 which claims priority to GB Patent Application Nos. 0706914.9 filed Apr. 10, 2007 and 0717888.2 filed Sep. 13, 2007, the entire disclosure of each being incorporated by reference herein.

FIELD OF THE INVENTION

The invention relates to recombinant adenoviral vectors which are capable of eliciting immunity against the pre-erythrocytic stage of the life cycle of the malaria parasite. In particular, the invention provides a recombinant simian adenoviral vector which encodes an antigen comprising the thrombospondin-related adhesion protein (TRAP), and also immunogenic compositions (e.g. vaccines) comprising the vector and methods of using such compositions.

BACKGROUND TO THE INVENTION

Malaria remains a major health problem in the world. It has been estimated that at least 3,000 million people, nearly half of the world's population, are living in malaria endemic areas and between 300 and 500 million clinical cases and about 1.5 million deaths are reported annually [1]. The development of an effective vaccine would be an important achievement to help decrease the problem of this disease. The pre-erythrocytic vaccination approach has shown some efficacy in clinical trials with immunity to this stage of the malaria life cycle directed towards both the sporozoite and subsequent intrahepatic schizont [2]. The cellular immune response has previously been shown to be important in pre-erythrocytic immunity with CD8+ T cells and IFNγ production playing a major role in protection against liver stage malaria [3].

The thrombospondin-related adhesion protein (TRAP) is an antigen expressed on the sporozoites which has previously been shown to induce protective CD8+ T cell responses [4]. TRAP has been extensively tested in vaccine clinical trials as a fusion protein with a multiepitope string containing additional B-cell, CD8+ and CD4+ T cell epitopes from several malaria antigens, known as ME.TRAP [5, 6].

Vaccine vectors based on plasmid DNA or modified vaccinia virus Ankara (MVA) encoding the ME.TRAP antigen have been tested in the field (Moorthy et al. (2004) PLoS, Med 1(2): e33) and shown to induce high frequencies of effector T cells when used in a prime-boost regime.

Nevertheless, there remains a need for improved anti-malarial vaccines which are capable of preventing natural infection with *Plasmodium falciparum* in human subjects as well as inducing stronger T cell responses, particularly of the CD8+ type. In clinical trials of ME.TRAP as an insert in both DNA and poxvirus vectors, such as MVA and fowlpox, responses have been predominantly of the CD4+ type which are probably less protective than CD8+ T cell responses.

Adenoviral vectors of the human serotype 5 have previously been used in a *P. yoelii* mouse model of malaria and have shown outstanding immunogenicity and significant protection after just a single dose [7]. However, one major limitation preventing the use of this serotype in humans is the ubiquitous presence of AdH5, with frequent childhood infections resulting in seroconversion. To circumvent the problem of pre-existing immunity to AdH5, there has been increased interest in the use of adenoviral serotypes of simian origin that do not circulate in human populations, with a number of studies demonstrating the ability of these vectors to elicit CD8+ T-cell responses in both mice and nonhuman primate models of SARS [8] and HIV [9, 10].

SUMMARY OF THE INVENTION

The present inventors have now shown that simian adenoviral vectors (particularly those derived from the chimpanzee adenovirus isolate AdCh63) encoding the ME.TRAP antigen can elicit outstanding CD8+ T-cell responses, as well as a high titer antibody response against TRAP, over a long period of time. Moreover, immunogenicity can be boosted by a subsequent administration of an MVA vector coding for the same transgene, and strong immunogenicity is observed in rhesus macaques, a species used as a good predictor of likely human immunogenicity. Immunogenicity has also been demonstrated in a Phase I human clinical study. Protective efficacy studied with the AdCh63 vector encoding ME.TRAP in a mouse challenge model was unexpectedly greater than with other adenoviral vectors. Efficacy in this mouse model is widely seen in-the field as being a useful and predictive indicator for humans.

In a first aspect the invention provides a recombinant replication-defective simian adenovirus vector which encodes an antigen comprising thrombospondin-related adhesion protein (TRAP) or at least one T cell epitope thereof.

In one embodiment the simian adenovirus vector comprises a simian adenovirus genome into which is stably integrated a transgene which encodes at least one antigen operably linked to regulatory sequences which direct expression of the transgene in mammalian cells, wherein the antigen comprises a thrombospondin-related adhesion protein (TRAP) or at least one T cell epitope thereof.

In one embodiment the simian adenoviral genome is the genome of a chimpanzee adenovirus vector.

In a specific non-limiting embodiment the simian adenoviral genome may be the genome of chimpanzee adenovirus isolate 63 (AdCh63). The vector AdC68, also known as AdC9, or the AdCh3 vector, or the AdC6 or AdC7 vectors may also be used, but the AdCh63 vector is preferred. Thus, the invention particularly relates to a recombinant replication-defective AdCh63 vector which encodes an antigen comprising thrombospondin-related adhesion protein (TRAP) or at least one T cell epitope thereof.

In all embodiments of the invention, the antigen encoded by the simian adenovirus vector may comprise or consist of ME.TRAP.

In a particular non-limiting embodiment the invention provides a recombinant replication-defective simian adenoviral vector (and particularly an AdCH63 vector) which encodes ME.TRAP, wherein expression of ME.TRAP is driven by the a regulatory sequence which comprises the promoter of the human CMV IE1 gene and a fragment of the 5' untranslated region of the human CMV IE1 gene including intron A (also referred to herein as the "long" HCMV promoter).

In a second aspect the invention provides an immunogenic composition comprising the simian adenovirus vector according to the first aspect of the invention admixed with one or more pharmaceutically acceptable vehicles, carriers, diluents or adjuvants.

In a related aspect, the invention provides a vaccine composition comprising the simian adenovirus vector according to the first aspect of the invention admixed with one or more pharmaceutically acceptable vehicles, carriers, diluents or adjuvants.

In particular non-limiting embodiments the invention provides an immunogenic composition or vaccine composition comprising a recombinant replication-defective simian adenoviral vector (and particularly an AdCH63 vector) which encodes ME.TRAP, wherein expression of ME.TRAP is driven by the "long" HCMV promoter. In a particular non-limiting embodiment the immunogenic or vaccine composition comprises said adenoviral vector formulated in 10 mM Histidine, 7.5% sucrose, 35 mM NaCl, 1 mM $MgCl_2$, 0.1% PS80, 0.1 mM EDTA, 0.5% ethanol, pH 6.6, which is suitable for intradermal administration to human subjects.

In a third aspect the invention provides a method of eliciting an immune response against thrombospondin-related adhesion protein (TRAP) in a human subject, which comprises administering to the subject an immunogenic composition or a vaccine composition comprising a recombinant simian adenoviral vector encoding TRAP (according to the first aspect of the invention) in an amount sufficient to elicit an immune response against TRAP in said subject.

In one embodiment the immunogenic or vaccine composition is administered as a single dose immunization.

In a fourth aspect the invention provides a method of eliciting an immune response against thrombospondin-related adhesion protein (TRAP) in a human subject, which comprises i) administering to the subject a priming dose of an immunogenic composition or a vaccine composition comprising a recombinant simian adenoviral vector encoding TRAP (according to the first aspect of the invention); and ii) administering to the same subject a boosting dose of an immunogenic or vaccine composition comprising a non-adenoviral vector which encodes an antigen comprising thrombospondin-related adhesion protein (TRAP),wherein the boosting dose is administered at least two weeks after the priming dose, In one embodiment the boosting dose may be administered eight weeks after the boosting dose.

One or more further boosting doses may be administered to the same subject if required in order to optimise the immune response elicited in that subject.

In one embodiment the non-adenoviral vector administered in step ii) is a recombinant pox virus vector, for example modified vaccinia Ankara (MVA).

In a fifth aspect the invention provides a product combination or kit comprising:

i) a priming composition comprising a simian adenovirus vector which encodes an antigen comprising TRAP, or at least one T cell epitope thereof; and ii) a boosting composition comprising a non-adenoviral vector, wherein the non-adenoviral vector also encodes an antigen comprising a thrombospondin-related adhesion protein (TRAP) or at least one T cell epitope thereof.

The priming composition preferable comprises a simian adenovirus vector which comprises a simian adenovirus genome into which is stably integrated a transgene which encodes at least one antigen operably linked to regulatory sequences which direct expression of the transgene in mammalian cells, wherein the antigen comprises a thrombospondin-related adhesion protein (TRAP) or at least one T cell epitope thereof.

In one embodiment the priming composition and the boosting composition may both encode identical antigens comprising a thrombospondin-related adhesion protein (TRAP) or at least one T cell epitope thereof.

In a specific non-limiting embodiment the priming composition and the boosting composition may both encode ME.TRAP.

In a further aspect the invention provides a recombinant replication-defective simian adenovirus vector encoding an antigen comprising TRAP, and in particular a simian adenovirus vector comprising a simian adenovirus genome into which is stably integrated a transgene which encodes at least one antigen operably linked to regulatory sequences which direct expression of the transgene in mammalian cells, wherein the antigen comprises a thrombospondin-related adhesion protein (TRAP) or at least one T cell epitope thereof, for use as a vaccine.

The invention also provides use of a recombinant replication defective simian adenovirus vector encoding an antigen comprising TRAP, and in particular a simian adenovirus vector comprising a simian adenovirus genome into which is stably integrated a transgene which encodes at least one antigen operably linked to regulatory sequences which direct expression of the transgene in mammalian cells, wherein the antigen comprises a thrombospondin-related adhesion protein (TRAP) or at least one T cell epitope thereof, in the manufacture of a medicament for use in eliciting an immune response to thrombospondin-related adhesion protein (TRAP) in a human subject.

The invention still further provides use of a recombinant replication-defective simian adenovirus vector encoding an antigen comprising TRAP, and in particular a simian adenovirus vector comprising a simian adenovirus genome into which is stably integrated a transgene which encodes at least one antigen operably linked to regulatory sequences which direct expression of the transgene in mammalian cells, wherein the antigen comprises a thrombospondin-related adhesion protein (TRAP) or at least one T cell epitope thereof, in the manufacture of a medicament for use as an anti-malarial vaccine.

BRIEF DESCRIPTION OF THE DRAWINGS

FIG. 1 schematically illustrates construction of an exemplary adenoviral vector according to the invention based on the chimpanzee adenoviral vector AdCh63 encoding the antigen ME.TRAP.

Figure 1A:
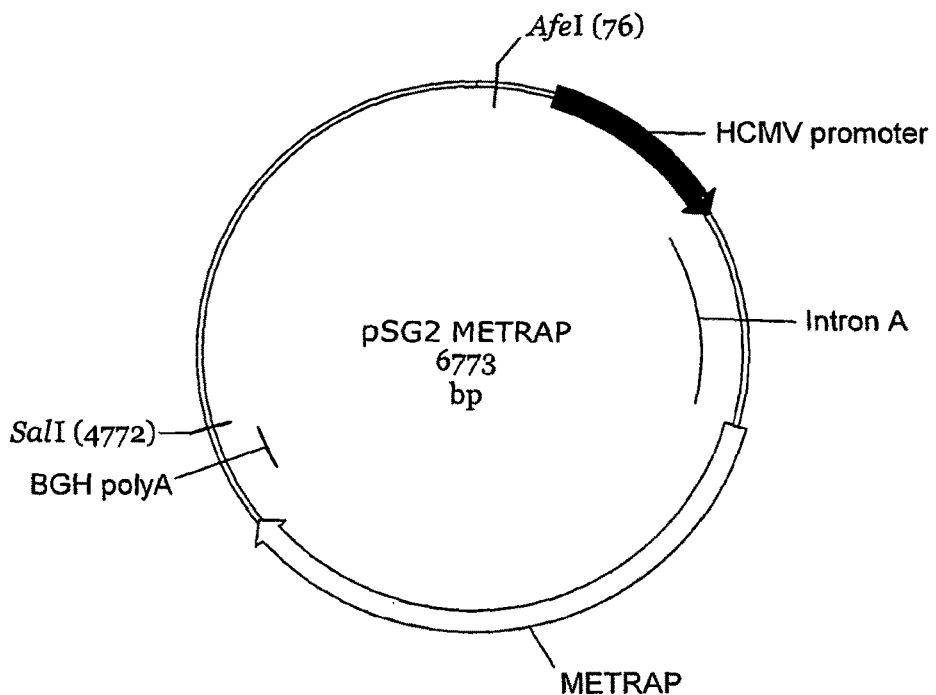
FIG. 1a shows the plasmid pSG2 ME.TRAP.
Figure 1B:
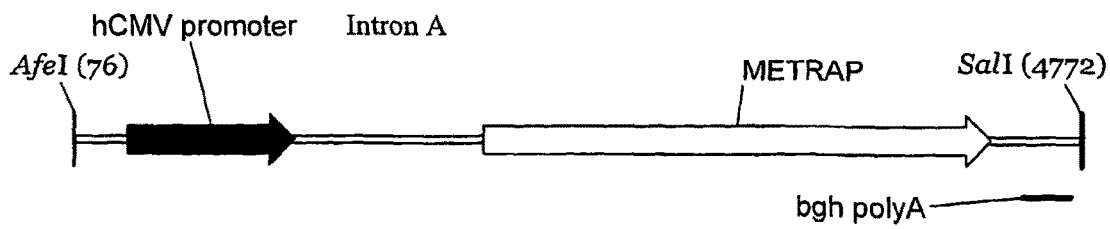
FIG. 1b shows a 4.7 kb fragment excised from pSG2 ME.TRAP by digestion with AfeI and SalI. This fragment contains the HCMV promoter, Intron A, ME.TRAP and BGHpolyA sequence.

BALE/c mice were initially immunized with adenoviral (5×10⁹ vp) vectors and subsequently boosted after 8 weeks with MVA (1×10⁷ pfu) coding for ME.TRAP. Mice were challenged after 14 (a), 63(b) and 182 (c) days by i.v. administration of 1000 sporozoites of *Plasmodium berghei*.

FIG. 6. Illustrates immunogenicity of AdCh63 ME.TRAP-prime, MVA ME.TRAP-boost regimes in Rhesus macaques. Macaques were immunized intramuscularly and intradermally with AdCh63 ME.TRAP (5×10¹⁰ vp) and boosted 8 weeks later with MVA ME.TRAP (2×10⁸ pfu). An ex-vivo IFNγ ELISPOT was performed in blood after the immunization a) Kinetics of the immune response upon Ad-prime and MVA-boost showing the overall ME.TRAP responses in blood. b) IFNγ response to peptide pools spanning the whole sequence of ME.TRAP at week 4 after priming and week 1 after boosting (c).

Figure 7:
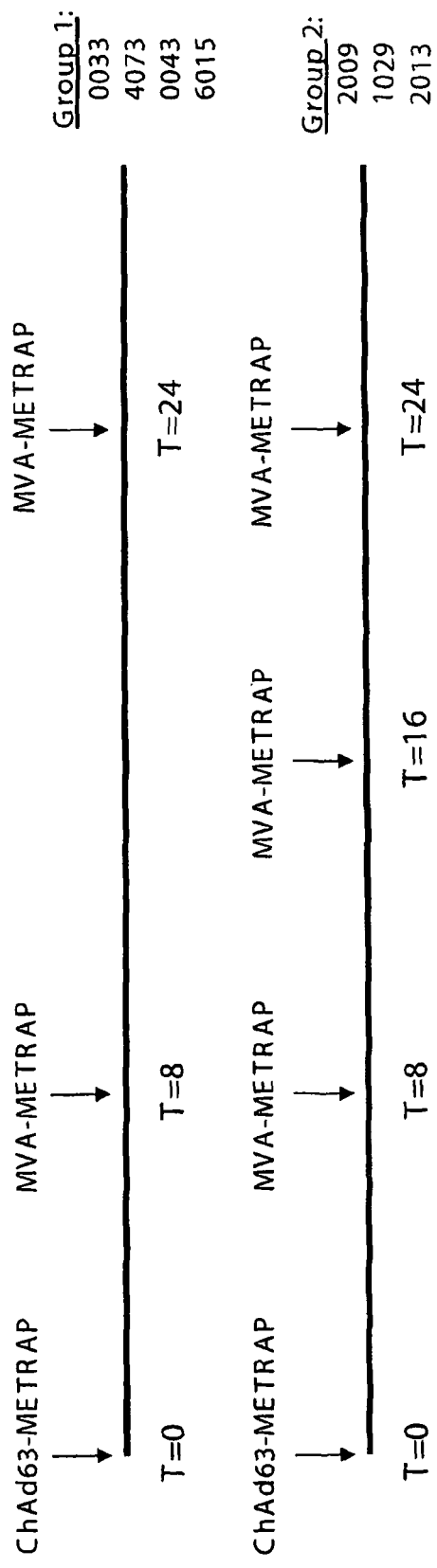

FIG. 7. Schematically illustrates two different AdCh63 ME.TRAP-prime, MVA ME.TRAP-boost regimes tested in rhesus macaques. Time (T) is given in weeks. In each case the priming vaccine was AdCh63 ME.TRAP (5×10¹⁰ vp administered intramuscularly or intradermally) and the boosting 8 weeks later with MVA ME.TRAP (2×10⁸ pfu administered intradermally).

Figure 8A:
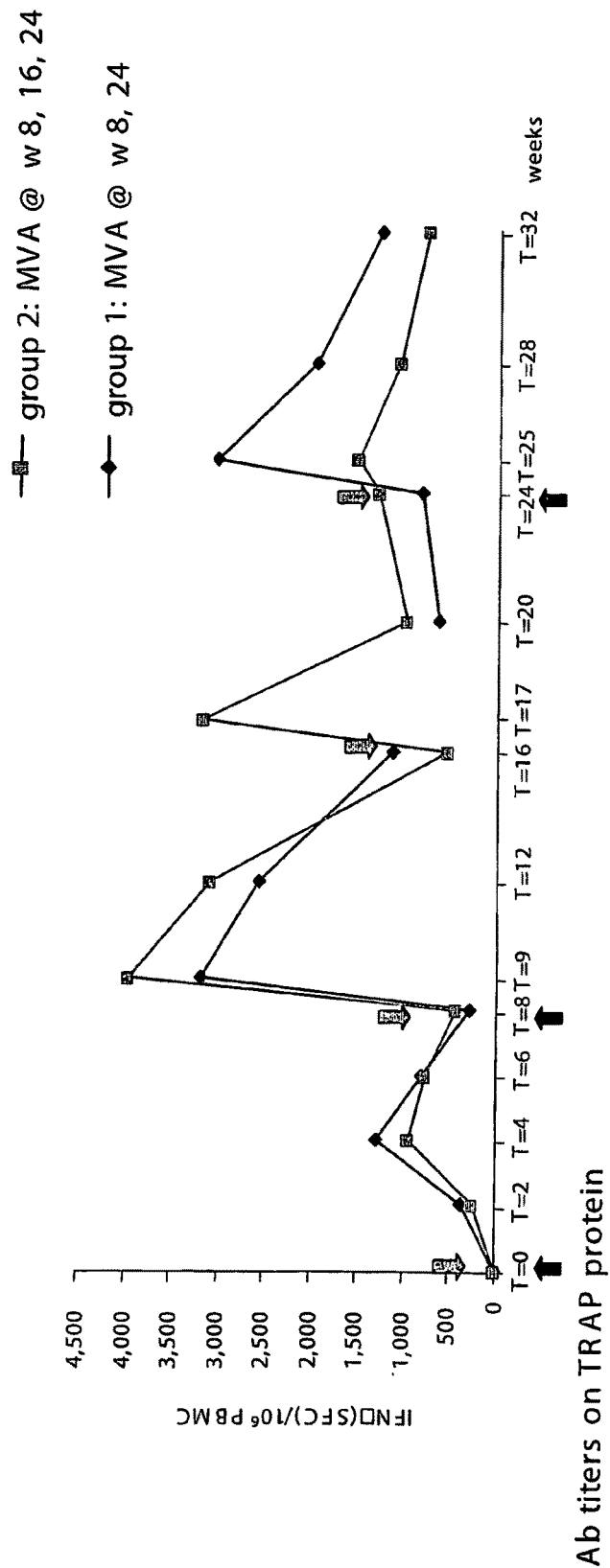
Figure 8B:
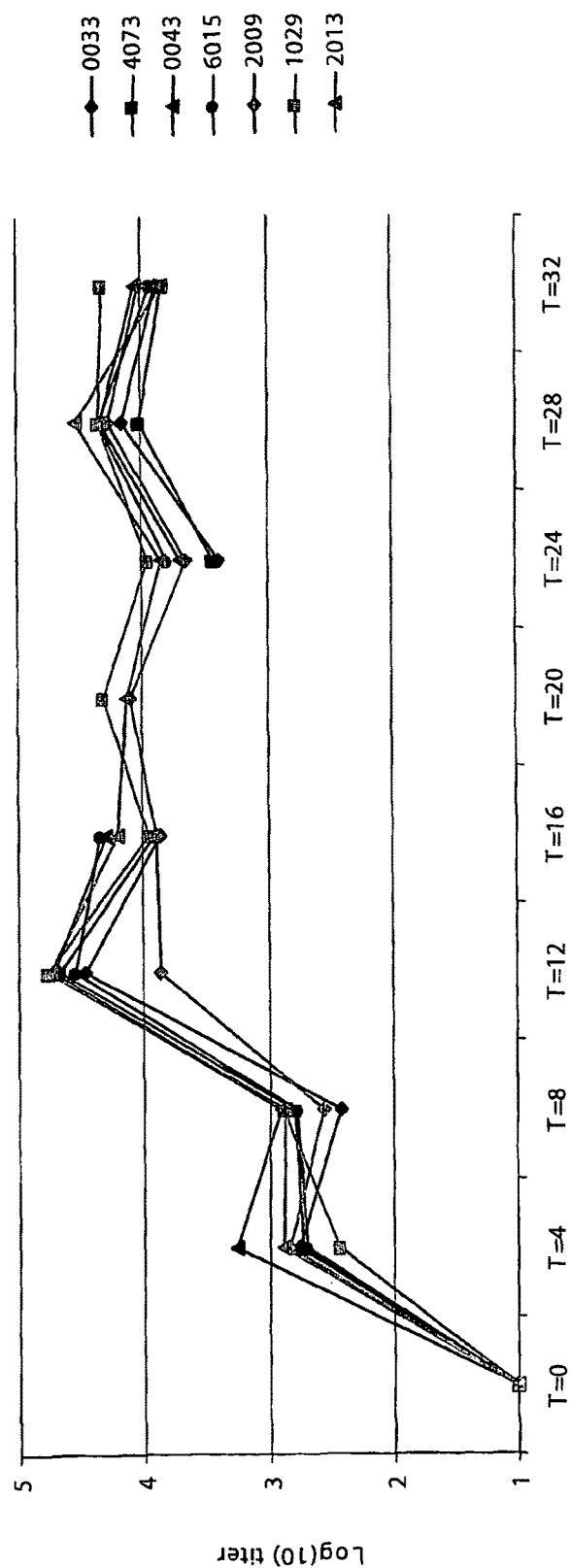

FIG. 8. Also illustrates immunogenicity of AdCh63 ME.TRAP-prime, MVA ME.TRAP-boost regimes in Rhesus macaques, comparing TRAP T cell response and antibody titers. Panel (a) shows TRAP T cell response determined using IFNγ ELIspot on TRAP peptide pools over the time course of the vaccination study described in the accompanying examples (T=time in weeks). Subjects in group 1 received boosting doses of MVA ME.TRAP at 8 and 24 weeks, whereas group 2 received boosting doses of MVA ME.TRAP at 8, 16 and 24 weeks. A single immunisation with AdCh63 ME.TRAP produced a strong T cell response of about 1000 SFU per million PBMC. Panel (b) shows the time course of antibody titer measured against TRAP protein for 7 individuals, demonstrating that strong antibody titers were induced by vaccination with AdCh63 ME.TRAP, and boosted with MVA ME. TRAP.

Figure 9:
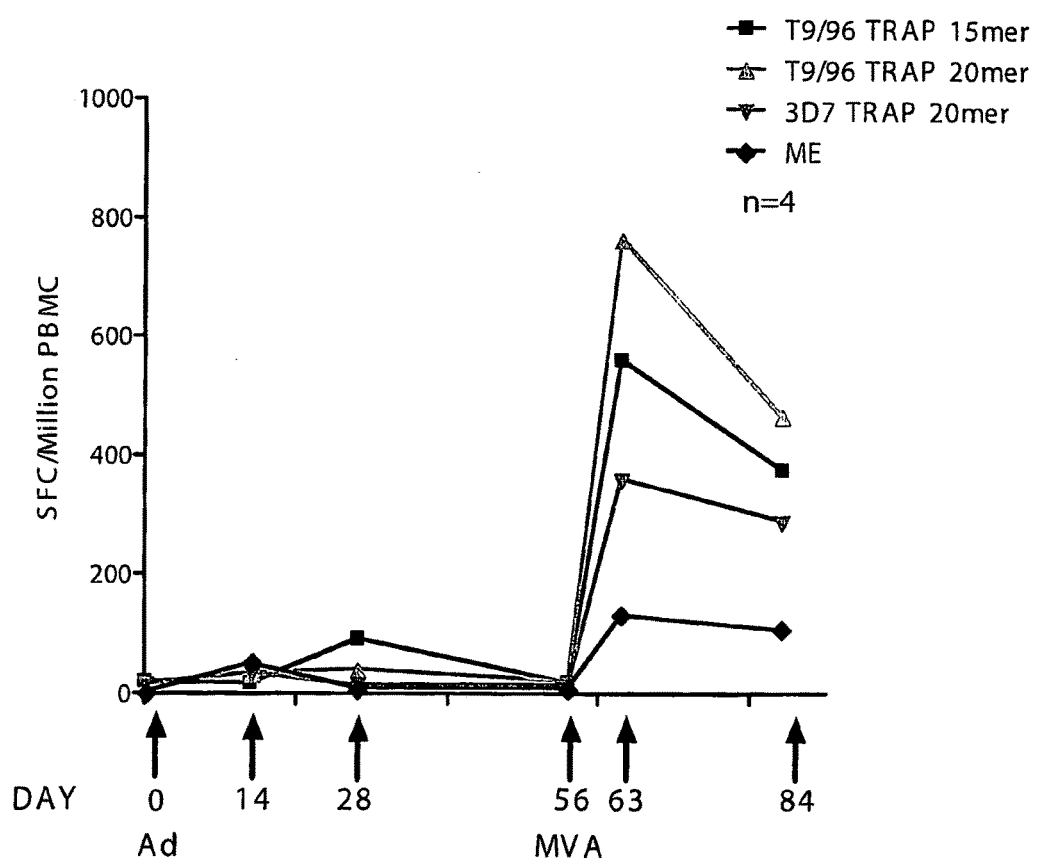

FIG. 9. Shows the time course of T cell immunogenicity in a phase I clinical test AdCh63 ME.TRAP in human subjects, assessed by IFNγ ELIspot to 15mer peptide pools overlapping the vaccine insert (T9/96 TRAP 15 mer), and to the same sequence with overlapping 20 mer peptides (T9/96 TRAP 20 mer). Also shown are the response to 20 mer peptides representing a heterologous strain of *P. falciparum* (3D7 TRAP 20 mer) and the response to a short string of mainly nonamer malaria peptide epitopes in the ME polyepitope string (Gilbert et al., Nature Biotech. 1997, Nov. 15, 1280-84) (ME).

DETAILED DESCRIPTION OF THE INVENTION

In the following paragraphs the various aspects of the invention are described in further detail. Any feature described as preferred in connection with one aspect of the invention is also preferred in relation to other aspects of the invention unless otherwise stated.

The present inventors have constructed simian adenovirus vectors which express a heterologous antigen comprising the pre-erythrocytic malarial (sporozoite) antigen thrombospondin-related adhesion protein (TRAP) and have observed that such vectors are capable of eliciting strong CD8+ T cell responses in two different animal models. The level of T cell response elicited using simian adenoviral vector to express the TRAP antigen was unexpectedly high, particularly when tested in a primate model, indicating that the combination of simian adenoviral vector and TRAP antigen is particularly potent in eliciting immunity to this pre-erythrocytic malarial antigen.

A major aspect of the invention is therefore the provision of a recombinant replication-defective simian adenoviral vector which encodes an antigen comprising TRAP or at least one epitope thereof (preferably at least one T cell epitope of TRAP). The recombinant replication-defective simian adenoviral vector will typically comprise a simian adenovirus genome into which is stably integrated a transgene which encodes at least one antigen operably linked to regulatory sequences which direct expression of the transgene in mammalian cells, wherein the antigen comprises a thrombospondin-related adhesion protein (TRAP) or at least one T cell epitope thereof.

Adenoviral vectors, and specifically simian adenoviral vectors, are generally known in the art. A number of replication-defective recombinant simian adenoviruses are described in WO 2005/071093, the contents of which are incorporated herein in their entirety by reference.

The simian adenoviral vectors of the invention typically comprise a simian adenoviral genome which is modified by stable insertion of a transgene expression cassette which comprises a nucleic acid sequence encoding a TRAP antigen operably linked to regulatory sequences which are capable of directing expression of the TRAP antigen in a mammalian cell.

The recombinant simian adenoviral vectors of the invention are typically "replication defective", meaning that they have been rendered incapable of replication because of a functional deletion, or complete removal, of a gene encoding a gene product essential for viral replication. By way of example, the vectors of the invention may be rendered replication defective by removal of all or a part of the E1 gene, and optionally also the E3 region and/or the E4 region. The native E4 region of the simian adenovirus may be replaced by that of a human adenovirus, e.g. Ad5E4orf6. The general features of "replication-defective" simian adenoviral vectors are known in the art, for example from WO 2005/071093, the contents of which are incorporated herein by reference.

In one particular, but non-limiting, embodiment the recombinant adenoviral vector of the invention may be based on the genome of the chimpanzee adenovirus isolate AdCh63. This particular viral serotype is known in the art (e.g. from WO 2005/071093) but has never before been described as a vaccine carrier for the pre-erythrocytic TRAP antigen of *Plasmodium* sp. The inventors have observed that the combination of the AdCh63 vector backbone expressing a TRAP antigen induces a spectacular CD8+ T cell response, and has the additional advantage of eliciting a strong TRAP-specific antibody (IgG) response.

The vector of the invention may express a full length TRAP antigen, or a fragment thereof which comprises at least one T cell epitope. Typically the fragment comprising at least one T cell epitope will be at least nine amino acids in length, and may be any length up to the full length of TRAP or ME.TRAP. For example, the fragment may be in the range of from 9 to 200, or from 9 to 100, of from 9 to 50 amino acids in length. The positions of T cell epitopes within the TRAP sequence have been described previously in the literature and will be well known to persons skilled in the art. Example T cell epitopes of TRAP are described in the following publications: Aidoo M, Lalvani A, Allsopp C E, Plebanski M, Meisner S J, Krausa P, Browning M, Morris-Jones S, Gotch F, Fidock D A, et al. Lancet. 1995; 345:1003-7; Flanagan K L, Plebanski M, Akinwunmi P, Lee E A, Reece W H, Robson K J, Hill A V, Pinder M. Eur J Immunol. 1999 June; 29:1943-54; and Flanagan K L, Plebanski M, Odhiambo K, Sheu E, Mwangi T, Gelder C, Hart K, Kortok M, Lowe B, Robson K J, Marsh K, Hill A V. Am J Trop Med Hyg. 2006 March; 74(3):367-75, the contents of which documents are expressly incorporated herein in their entirety by reference for the purpose of describing known T cell epitopes of TRAP.

The TRAP antigen may be derived from any *Plasmodium* sp., but will typically be a TRAP antigen from a strain of *Plasmodium falciparum*. The TRAP antigen sequence may be from any *Plasmodium falciparum* strain, but in a particular (non-limiting) embodiment the TRAP antigen is from *Plasmodium falciparum* strain T9/96. The TRAP antigens of different strains of *Plasmodium falciparum* display a high degree of amino acid sequence identity (typically greater than 90% across the full length TRAP sequence). Thus, it is contemplated to use any TRAP amino acid sequence which shares greater than 90%, greater than 95% or greater than 99% amino acid sequence identity with the TRAP antigen of *Plasmodium falciparum* strain T9/96.

The TRAP antigen (or T cell epitope fragment thereof) may be expressed alone or in combination with additional polypeptide sequences, for example as a fusion protein. These additional polypeptide sequences may comprise B-cell, CD8+ T cell or CD4+ T cell epitopes, and specifically B-cell or T cell epitopes from *Plasmodium falciparum* antigens other than TRAP. A particularly advantageous combination is the construct denoted ME.TRAP, which comprises a full length TRAP antigen fused to a multi-epitope string of B-cell, CD8+ T cell and CD4+ T cell epitopes from other pre-erythrocytic *Plasmodium falciparum* antigens, (5,6). The ME.TRAP antigen described in the literature (and shown in SEQ ID NO:2) contains the full length TRAP sequence taken from *Plasmodium falciparum* strain T9/96. However, it will be appreciated that the TRAP portion of this ME.TRAP construct may be replaced with TRAP sequences taken from other strains of *Plasmodium falciparum*. Skilled readers will also appreciate that the TRAP sequence (and/or the ME sequence) may be modified by one or more amino acid substitutions, insertions or deletions without substantially altering T cell (or B cell) immunogenicity.

In one specific, non-limiting embodiment the ME.TRAP antigen may comprise or consist of the amino acid sequence shown as SEQ ID NO:2. Other suitable TRAP antigen sequences are described by Robson K J, et al. Nature. 1988; 335:79-82, incorporated herein by reference. The ME epitope string is described by Gilbert S C, et al., Nat Biotechnol. 1997; 15(12):1280-4, incorporated herein by reference.

The regulatory sequences directing expression of the TRAP antigen may include transcription initiation sequences, promoter sequences or enhancer sequences, and combinations thereof. The promoter sequence is typically a heterologous promoter (with respect to both the adenovirus and the expressed antigen) and can be any promoter which is recognised by eukaryotic RNA polymerase (e.g. RNA polII).

A preferred promoter is the immediate early (IE1) promoter of human cytomegalovirus (CMV), which is described by Chapman et al. NAR, 19: 3979-3986, incorporated herein in its entirety by reference. This promoter may be used in a "long" form which includes a fragment of the 5' untranslated region of the IE1 gene comprising the intron A sequence, or in a "short" form which lacks the intron A sequence. The "long" CMV promoter is generally preferred and will typically exclude exon B. However, it should be understood that the invention is not limited to the use of the "long" HCMV promoter to direct expression of the TRAP antigen. Other heterologous promoters which direct a suitable level of expression of the antigen may be used, including promoters which expression levels substantially equivalent to those achieved using the HCMV "long" promoter. Suitable promoters include, for example, the murine CMV promoter, Rous Sarcoma virus (RSV) promoter, SV40 early/late promoters and the beta-actin promoter.

The transgene expression cassette (encoding the antigen comprising TRAP) will typically also include a heterologous transcription terminator sequence. Any suitable RNApolII terminator sequence may be used, for example the BGH poly A sequence. The combination of HCMV "long" promoter and BGH polyA sequence is particularly advantageous and is preferred for use with the AdCh63 vector backbone.

The transgene expression cassette (encoding the antigen comprising TRAP) will typically be inserted into the E1-deleted region of the simian adenoviral genome. However, it should be understood that the precise location of the insertion site and the orientation of the transgene expression cassette in the vector are not critical provided that 1) the transgene expression cassette is functional, in the sense that it is capable of directing expression of the antigen comprising TRAP following insertion into the adenoviral genome and 2) insertion of the transgene does not prevent replication and/or packing of the adenoviral vector into infective viral particles in a suitable host cell line.

The simian adenovirus vectors of the invention are typically supplied and used as infectious viral particles comprising the recombinant adenovirus genome encoding the TRAP antigen. Replication-defective adenoviruses can be grown in tissue culture to produce high titres of infectious viral particles, using cell lines that provide the missing gene products essential for viral replication and packaging in trans. The adenoviral backbone (genome) sequences may be cloned into bacterial plasmid vectors in order to facilitate cloning and manipulation using standard recombinant DNA techniques. Such plasmids represent "molecular clones" of the corresponding adenovirus vector, and contain the entire recombinant adenoviral genome. Following restriction enzyme digestion of the plasmid vector to remove bacterial sequences and expose the inverted terminal repeats, the resulting nucleic acid may be used to transfect a suitable host cell line which supplies the essential gene function deleted from the viral genome sequence (e.g. the E1 gene product), this generating pure recombinant virus particles. A suitable example is the cell line HEK 293, which supports the growth of E1-deleted adenoviruses. Another suitable cell line is that called PerC6.

Although the invention primarily relates to recombinant simian adenoviral particles which can be administered in immunogenic compositions, e.g. vaccines, it is to be understood that the corresponding plasmid vectors, which comprise the simian adenoviral backbone with a stably integrated TRAP (or ME.TRAP) expression cassette in plasmid vector form, also form part of the invention. Such plasmid vectors are useful in the production of high titer stocks of adenoviral particles comprising the recombinant adenovirus genome encoding the TRAP (or ME.TRAP) antigen.

Immunogenic Compositions

The invention also provides immunogenic compositions comprising the simian adenovirus vector according to the first aspect of the invention. Such compositions typically comprise the simian adenovirus vector in the form of infective adenoviral particles admixed with one or more pharmaceutically acceptable vehicles, diluents, carriers or adjuvants.

In one embodiment the composition may be a vaccine composition which is suitable for human administration and which can be used to elicit a protective immune response (such as by CD8+, often cytotoxic, T cells) against at least the TRAP antigen.

The preferred features of the simian adenoviral vectors described in connection with the first aspect of the invention apply also to the compositions of the invention.

The compositions of the invention will typically be formulated as liquid dosage forms comprising adenoviral particles in a suitable liquid carrier, for example an aqueous carrier such as 10 mM Histidine, 7.5% sucrose, 35 mM NaCl, 1 mM $MgCl_2$, 0.1% PS80, 0.1 mM EDTA, 0.5% ethanol, pH 6.6, endotoxin-free PBS or any other suitable carrier. Preferred dosage forms are formulated for intramuscular or intradermal administration, although other routes of administration, such as oral, intravenous, mucosal, transdermal etc. are not excluded. Immunogenic or vaccine compositions intended for human administration typically contain viral particles at a titre in the range of from $1-3\times10^{11}$ vp/mL.

Methods of Eliciting Immune Response

Compositions comprising the simian adenoviral vector of the invention may be administered to human subjects in order to elicit an immune response against the encoded TRAP antigen. The inventors have shown that vectors according to the invention (and in particular AdCh63 or AdC9 vectors encoding the ME.TRAP antigen) can elicit a strong CD8+ T cell response in animal models. In particular, the protective efficacy shown with the AdCh63 Vector encoding ME.TRAP in a mouse challenge model is quite unexpectedly greater than with other adenoviral vectors. Efficacy in this model is widely seen in the field as being a useful and predictive indicator for humans and thus the vaccine comprising AdCh63 encoding ME.TRAP will be useful in protecting humans against malaria. Indeed, the inventors have already demonstrated that an example vaccine comprising AdCh63 encoding ME.TRAP is immunogenic in humans.

The invention therefore provides for administration of the compositions according to the invention (and in particular compositions comprising the AdCh63 vector encoding the ME.TRAP antigen) to human subjects in either a single immunization or as part of a broader dosing regimen, for example a prime-boost regime.

The human subjects receiving immunisations with the simian adenoviral vectors of the invention may be any human subjects that it is desired to immunise against malaria.

For single immunization regimes, subjects will typically receive a dose in the range of from $1\times10^8$ to $5\times10^{10}$ viral particles. This dose will generally be administered intradermally, but other treatment regimes involving alternative dosages and routes of administration are not to be excluded.

Prime-boost regimes will typically involve administration of a priming dose of recombinant simian adenovirus expressing the antigen comprising TRAP (and in particular ME.TRAP) at a first time point, followed by administration of a boosting dose of a non-adenoviral vector encoding an antigen comprising TRAP (or ME.TRAP) at a second time point. The first and second time points will be separated by at least two weeks, and typically by approximately 6 weeks.

The non-adenoviral vector used to administer the boosting dose can be any non-adenoviral vector encoding an antigen comprising TRAP (or ME.TRAP). Suitable examples include viral vectors, particularly recombinant pox virus vectors (e.g. MVA), and plasmid DNA vectors.

A preferred (but non-limiting) combination utilises recombinant AdCh63 encoding the ME.TRAP antigen for the priming dose and MVA encoding ME.TRAP for the boosting dose (e.g. at a dose in the range of from $1\times10^7$ to $1\times10^8$ pfu). In a preferred (but again non-limiting) regime, both doses are administered intradermally and the priming and boosting doses are separated by a period of 8 weeks.

The T cells induced by the vaccine and vaccination regimes described herein may be useful for malaria prevention or treatment. But they also have other applications. They may be used to generate reagents of use in malaria diagnostics such as in the use of T cells to diagnose malaria infection. Or the T cells used may be of value in T cell transfer protocols for malaria immunotherapy. Also the ability of a n individual to generate a sufficient immune responses after vaccination may be used as a measure of immunocompetence, for the exclusion of specific immune or genetic defects.

The invention will be further understood with reference to the following non-limiting experimental examples.

Example 1

Production of AdC1163ME.TRAP Vector

AdCh63 ME.TRAP is a replication defective simian adenoviral vector expressing ME.TRAP to be used for vaccination to prevent malaria.

AdCh63 ME.TRAP, consists of the simian adenovirus, chimpanzee adenovirus serotype 63, containing a sequence of genes which express a series of known cytotoxic T lymphocytes, (CTL), epitopes from *Plasmodium falciparum* pre-erythrocytic stage antigens fused to a complete pre-erythrocytic stage antigen, Thrombospondin Related Adhesion Protein (TRAP).

The individual CTL epitopes which constitute the 'multiple epitope' part of ME.TRAP, represent a variety of potentially protective target antigens and are included to ensure an immune response to the vaccine in the majority of the population vaccinated. TRAP is an abundant pre-erythrocytic stage antigen. Human volunteers immunised with irradiated sporozoites and protected against malaria develop T cell responses against TRAP making it a strong candidate for inclusion in a malaria vaccine.

The nucleotide sequence of the vaccine insert is shown as SEQ ID NO:1.

Plasmid pChAd63 ME.TRAP was used as the starting material for AdCh63 ME.TRAP production. To produce this plasmid a ME.TRAP expression cassette was cloned into a linearised pre adeno-acceptor vector via homologous recombination. Construction of this plasmid is illustrated schematically in FIG. 1.

The plasmid pSG2 ME.TRAP (FIG. 1a) was cleaved with AfeI and SalI to excise a 4.7 Kb fragment containing the HCMV promoter, ME.TRAP and BGHpolyA sequence.

Figure 1C:
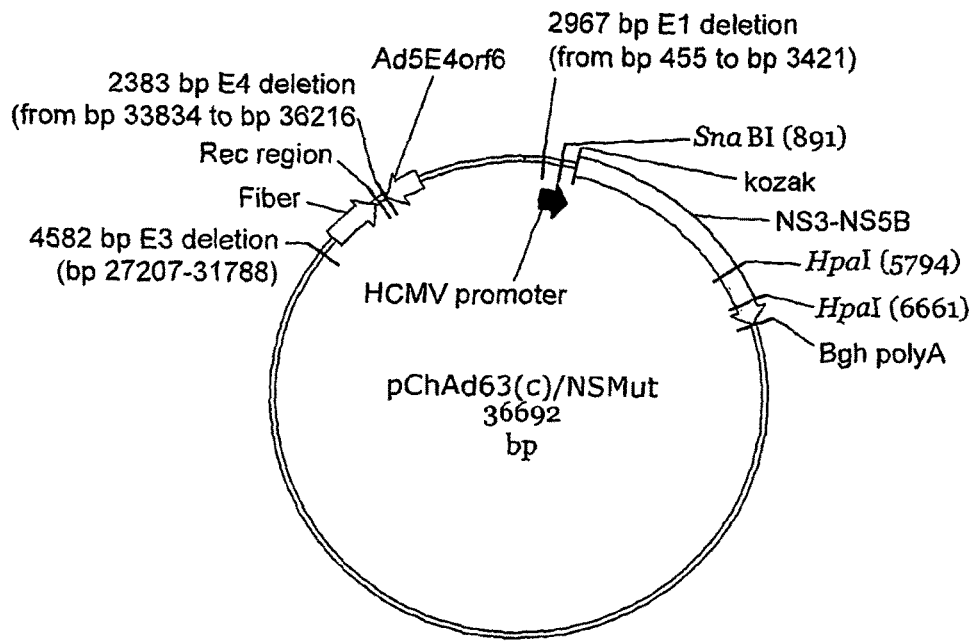
FIG. 1c illustrates the preChAd63NSmut acceptor vector carrying the non structural region (NS) of hepatitis C virus under control of HCMV and BGHpA.

The resulting ME.TRAP 4.7 Kb fragment (FIG. 1b) which also contains the HCMV promoter, Intron A and the BGH polyA sequence was recombined into a preChAd63NSmut acceptor vector carrying the non structural region (NS) of hepatitis C virus under control of HCMV and BGHpA (FIG. 1c). The pChAd63 vector is derived from the wild type Chimp Adenovirus 63 genome cloned in a plasmid vector carrying the following modifications in different regions of pChAd63 viral backbone:
1) deletion of the E1 region (from bp 455 to bp 3421) of the viral genome
2) deletion of the E3 region from bp 27207 to bp 31788
3) deletion of the E4 region from bp 33834 to bp 36216
4) insertion of the Ad5E4orf6 from bp 33319 to bp 34200

The acceptor vector, ChAd63(c) NSmut was linearised by cleaving with HpaI and SnabI. The ME.TRAP cassette was cloned in to the pre-adeno vector by homologous recombination in E. coli. BJ 5183 cells were co-transformed with ~30 ng of linearised acceptor vector (ΔHpaI, ΔSnabI) and ~100 ng of digested pSG2 ME.TRAP (ΔAfeI, ΔSalI). Recombination occurred between the 4.7 kb fragment and the pre adeno ChAd63NSmut acceptor vector resulting in the insertion of the 4.7 kb fragment (containing the HCMV promoter, the ME.TRAP gene and the BGH polyA sequence) into the adenoviral vector, exploiting the homology existing between HCMV promoter and BGH polyA sequences. Positive clones were identified by restriction digestion analysis with HindIII and EcoRI.

Figure 1D:
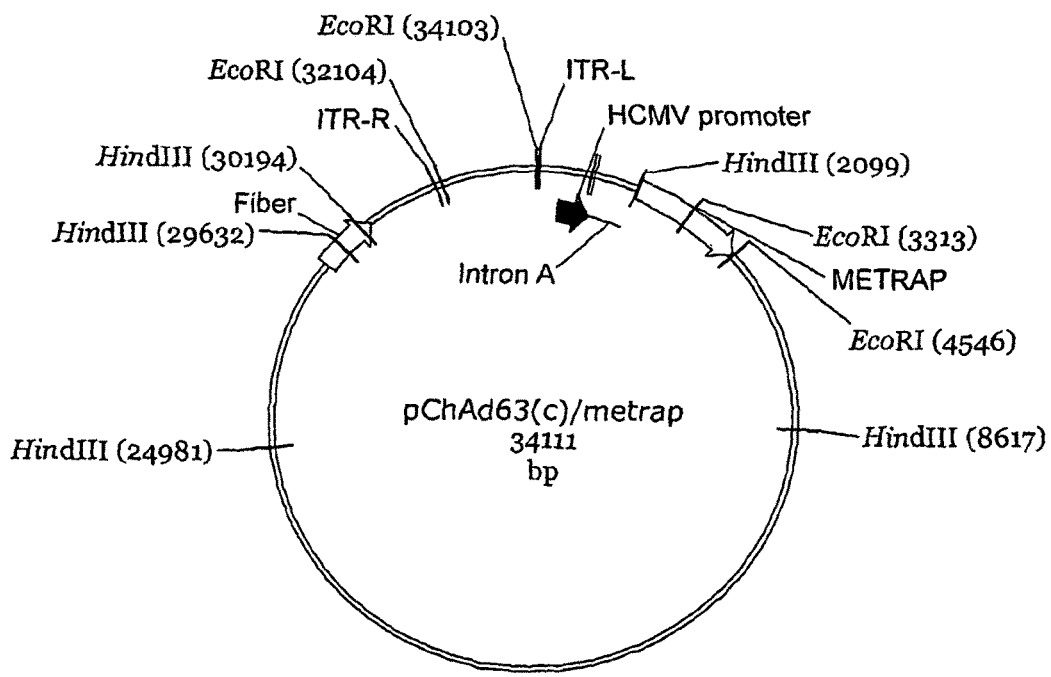
FIG. 1d illustrates the pre-plasmid pChAd63 containing the ME.TRAP antigen.

FIG. 1d is a map of the novel ChAd63 vector containing the ME.TRAP antigen. HindIII and EcoRI sites are shown. Confirmation of the identity of plasmid DNA was obtained by restriction enzyme analysis and sequencing. The expected HindIII-EcoRI restriction enzyme profiles were observed on agarose gel electrophoresis for ME.TRAP containing fragments. Sequence analysis was performed with different oligos confirming that the sequence of the ME-TRAP insert was correct.

Manufacture of the Primary Virus Stock, (PVS)
Preparation of HEK 293 Cells
↓
Linearisation of plasmid DNA
↓ transfection
Initiating Adenovirus infection
↓
Harvesting Adenovirus The Human Embryonic Kidney 293 (HEK 293) cell line is a permanent line of primary human embryonal kidney transformed by sheared human adenovirus type 5 DNA. The cells are particularly sensitive to human adenoviruses and will support the growth of E1A deleted replication deficient adenoviruses. HEK 293 cells were obtained from Bio Reliance, Todd Campus, West of Scotland Science Park, Glasgow G20 OXA.

The HEK 293 cell line was cultured as adherent cells. The cells were grown without antibiotics in DMEM supplemented with glutamine and 10% qualified foetal bovine serum, (FBS) in sterile conditions.

To produce the PVS, log phase HEK 293 cells were transfected with 5 μg of PmeI linearised plasmid DNA using the cationic liposome transfection reagent chemically defined, Lipofectamine, 2000, from Invitrogen (18 hours post seeding).

The restriction enzyme PmeI and specific buffer were purchased from New England Biolabs (NEB). The BSA in this buffer was defined as of US origin. Four units of PmeI (10,000U/mL) were used to linearise 1 μg of DNA. Sterile water was used for dilution. Dulbecco's modified Eagles medium, (DMEM) without foetal bovine serum, (FBS) was used for the transfection stage (the presence of FBS reduces the transfection efficiency). The transfected cells were harvested on day 10 when maximum cytopathic effect (CPE) was observed. The virus was harvested from the cells by three rounds of freeze thawing and pooled with the cell supernatant in 10% sterile glycerol with a final volume of 4.1 mL. Vials of PVS were snap frozen and stored at −80° C. A retest date of 6 months was assigned to this stock.

Manufacture of Pre Working Vector Stock

A single vial of HEK 293 cells was thawed and expanded in

DMEM plus glutamine containing 10% FBS to generate after 5 passages, 2 Cellbind rollers of evenly dispersed adherent cells. On the day of infection, the cells in 1 roller were suspended using recombinant trypsin and counted. The cell density was $1.06 \times 10^5$ cells/cm$^2$. The cells in the second roller were infected with primary virus stock at a multiplicity of infection (MOI) of 0.64 pfu/cell in 113 mL of inoculum. The required amount of stock virus (1.25 mL) was thawed on wet ice and diluted to 115 mL with cell culture medium, (DMEM plus glutamine and 2% FBS).

Roller bottles were rolled once manually then placed on a roller bank rotating at 0.1 rpm, in an incubator set at 37° C., for 48 hours. The roller bottles were checked daily for the presence of CPE. Typical CPE is accompanied by rounding of the cells. The control cell cultures are checked for the absence of CPE.

Virus-infected roller bottles were harvested after a single round of virus replication and with the appearance of total CPE (48 hours). The virus-infected cells were gently resuspended in the culture medium to form a cell suspension which was then pelleted by centrifugation for 15 minutes at 2000 rpm at 20° C. The supernatant was removed and the cell pellet was resuspended in 8.0 mL of cell lysis buffer, (10 mM Tris, 135 mM NaCl, 1 mM MgCl, pH 7.9 prepared in CBF purified water). The cell pellet was then transferred to a 50 mL polypropylene tube. The cell pellet was subjected to three rounds of freeze thawing (frozen in an IPA/dry $CO_2$ bath and then thawed in a 37° C. water bath). The cell lysate was clarified by further centrifugation at 3000 rpm for 30 minutes at 4° C. The supernatant (cell lysate) was snap frozen at −80° C. in small aliquots. A sample was taken from the cell lysate for infectious titre ($3.34 \times 10^8$ pfu/mL). Samples of infected and uninfected cell supernatant (both 100 mL) were analysed for bioburden (both negative).

Manufacture of Working Vector Stocks (WVS) 1 and 2

The pre working vector stock (pre WVS) was used to manufacture the working vector stock 1 (WVS1) and WSV1 was used to manufacture WVS2. Both involved a single round of virus replication in HEK 293 cells evenly adherent in Cellbind roller bottles. The size of WVS2 is calculated such that a batch production lot uses ≤10% of total WVS2. For WVS1, 14 rollers of HEK 293 cells at a cell density of $1.29 \times 10^5$/cm$^2$ were used for virus expansion and for WVS2, 29 rollers at a cell density of $1.54 \times 10^5$/cm$^2$ were used. The manufacturing specification for both WVS1 and WVS2 was the same. The viral inoculum (Pre WVS or WVS1 respectively) was diluted with DMEM plus glutamine and 2% FBS to 113 mL/roller for WVS1 and to 20 mL/roller for 2 hours then to 113 mL/roller final for WVS2. The final MOIs were 1.01 for WVS1 and 8.6 pfu/cell for WVS2 respectively). Bottles were rolled once manually then placed on a roller bank at 0.1 rpm, at 37° C. for 48 and 71 hours respectively.

The roller bottles were checked daily for the presence of CPE. A negative control roller containing uninfected HEK 293 cells was included in both procedures for comparison and for counting cells.

WVS1 was harvested 48 hours post infection whilst WVS2 was harvested at 71 hours post infection. Virus-infected cells were gently resuspended in the cell supernatant to form a cell suspension which was then decanted into centrifuge tubes and pelleted by centrifugation for 15 minutes at 2000 rpm at 20° C. The cell supernatants were removed and each cell pellet resuspended in 8.0 mL of cell lysis buffer, (10 mM Tris, 135 mM NaCl, 1 mM MgCl, pH 7.9) per roller. The cell pellet suspensions were then pooled into polypropylene tubes. The tubes underwent three rounds of freeze thawing (frozen in an IPA/dry $CO_2$ bath and then thawed in a 37° C. water bath). The resulting cell lysate was clarified by further centrifugation at 3000 rpm for 30 minutes at 4° C. The supernatant (cell lysate) containing the virus (WSV1 or WSV2) was pooled, sampled, aliquoted and snap frozen at −80° C. Final volumes of 112 mL and 236 mL for each stock were prepared.

Manufacture of the Bulk Harvest Clinical Lot of AdCh63 ME.TRAP

WVS 2 was used to manufacture three bulk harvest lots of AdCh63 ME.TRAP. Each lot consists of a single round of virus replication from WVS2. The procedure was similar to the manufacturing of the WVS2 as described above with an initial inoculation of 20 mL/roller for 2 hours followed by top up to a final volume of 113 mL/roller but had the addition of Benzonase after the first freeze/thaw cycle during cell lysis. The viral inoculum (WVS2) was diluted with DMEM containing 2% FBS and glutamine as previously described and was added into the HEK 293 roller bottles in 20 mL at an MOI of 2-3 pfu/cell). Bottles were rolled once manually then placed on a roller bank rotating at 0.1 rpm, in an incubator at 37° C. for 71 hours total. The roller bottles were checked daily for the presence of CPE and the virus-infected roller bottles were harvested after the appearance of total CPE. The virus-infected cells were gently resuspended in the culture medium to form a cell suspension. A 2.5 mL sample of the cell suspension and supernatant was removed from each roller and pooled. It was labelled as 'pre bulk harvest pool lot 1, 2 or 3. These 'bulk harvest' samples were taken for final pooling to generate bulk harvest sample for in process external testing of adventitious virus and for reverse transcriptase. The remaining suspension was then pelleted by centrifugation for 30 minutes at 2000 rpm at 20° C. The supernatants were removed and each cell pellet was resuspended in 8.0 mL of cell lysis buffer, (10 mM Tris, 135 mM NaCl, 1 mM MgCl, pH 7.9). The cell pellet suspensions were then pooled and dispensed into polypropylene tubes. The tubes underwent one round of freeze thawing (frozen in an IPA/dry $CO_2$ bath and then thawed in a 37° C. water bath). The minimum freeze time was 30 min. Benzonase was then added to degrade residual host cell DNA prior to purification (1500 units per 8 mL cell lysate). The cell lysate was incubated with Benzonase for 25-35 minutes at 20° C.±2° C. on a gyro rocker set at full speed after which a further two rounds of freeze thawing took place as previously described. The cell lysate was clarified by further centrifugation at 3000 rpm for 30 minutes at 4° C. The cell lysate supernatant was removed using a sterile pipette to measure the volume pooled, aliquoted and snap frozen at −80° C.

Downstream Processing to Prepare Purified Harvest Lot

Thaw BHL (54-128 mL)
↓
CsCl step gradient (1 or 2 runs/lot)
↓
CsCl equilibrium gradient (1 run/lot)
↓
Formulation (buffer exchange)
↓
Dilution and aggregate filtration (0.45μ)
↓
Snap freeze as a single purification lot Adenovirus particles have a distinct density in cesium chloride (CsCl) allowing their purification from the majority of contaminating viral and host cell proteins and DNA by density gradient ultracentrifugation in a Beckman Optima ultra centrifuge. Viral particles lacking packaged DNA (empty capsids) can be separated from complete virions as they have a lower density. Typically, following step gradient ultra-centrifugation a lower band of 'infectious' viral particles is seen with a band above it containing empty capsids. The harvest from the first step gradient is further purified by equilibrium CsCl density gradient ultracentrifugation for 20h. Purification lot size was constrained by the volume of bulk harvest that the centrifuge tubes and rotor (Beckman SW40) could hold. The size of the bulk harvest lot aliquots had been chosen such that the volume was suitable for transfer to this process and an appropriate volume of bulk harvest was thawed at the start of each purification lot. The virus harvest from between 1 and 2 preliminary step gradient centrifugation runs was used as the starting material for the second equilibrium centrifugation step. Thus the purification of the bulk harvest lots was performed in a series of repetitive sanitary processes. In total an initial small lot (for toxicity and stability studies) and 10 purification lots were prepared from the 3 bulk harvest lots.

Discontinuous CsCl Ultracentrifugation

A step gradient was prepared manually in 14 mL Ultraclear centrifuge tubes (Beckman) using 3 different densities of CsCl. The cesium chloride solutions were prepared in 10 mM Tris pH7.9 in CBF purified water. Initially 2 mL of 1.25 g/L CsCl solution was added to each tube and underlayered with 2 mL of 1.35 g/L CsCl. Finally the solution of greatest density of CsCl (0.5 mL of 1.50 CsCl) was underlayered. Step gradients were prepared using chilled solutions within 1 hour of use.

Individual samples of bulk harvest lot cell lysate were thawed in cold water (4-10° C.). Approximately 8.5 mL of cell lysate was manually layered on top of the CsCl gradient. The tubes were promptly (<1 hour) centrifuged at 180,000 g for 3 hours. An upper area of cell debris, a diffuse band of empty capsid material and a lower sharp band of infectious virus were separated during centrifugation. The lower band was harvested by piercing the side of each tube with a 16G horizontal needle attached to a 1 mL syringe. On average 0.6 mL of virus was collected per tube and pooled and stored if required at a 4-10° C. The maximum hold time was 4 hours.

Equilibrium CsCl Ultracentrifugation

Identical centrifuge tubes were used to perform equilibrium ultracentrifugation. These were initially filled with 6 mL of a CsCl density of 1.35 and overlayered with 1.0-1.5 mL of the virus pool harvested from the first ultracentrifugation steps. The top up buffer was phosphate buffered saline prepared in water for injection. The virus was centrifuged at 150,000 g for 20 hours at 10° C. This resulted in a diffuse faint upper band and a lower sharp band of intact virus particles. Two faint bands either side of the sharp band could also be visualised. The main sharp band of infectious virus particles was harvested using either a 16G horizontal needle and syringe as before. Between 0.5 and 1.0 mL of virus was harvested per tube and stored at 4-10° C. in a cold box for a maximum of 2 hours before final formulation by buffer exchange.

Formulation into Final Buffer

The CsCl purified pool of virus was buffer exchanged into final formulation buffer (A438) via chromatographic desalting on Sephadex G25 using disposable polypropylene ready poured PD-10 columns containing 8.3 mL of Sephadex G25 in water containing 0.15% Kathon as a biocide (Amersham Biosciences division of GE Healthcare). Conditions for a water wash of 6 column volumes prior to sanitisation were established that removed >99.5% of Kathon from the column eluate.

After washing, the columns were then sanitised for a minimum 20 minutes with 0.5M sodium hydroxide and five column volumes of phosphate buffered saline were used to neutralise the sodium hydroxide. The columns were finally washed into formulation buffer: (3 column volumes) Formulation buffer (A438): 10 mM Histidene, 35 mM NaCl, 1 mM MgCl. 0.1 mM EDTA, 0.5% (v/v) ethanol, 7.5% sucrose, 0.1% PS80 pH 6.6 was prepared using water for injection. Conditions were established for the virus sample (<1.5 mL) and collection volumes (<2.25 mL) that resulted in a final CsCl concentration in the final product maximum patient dose of >6 logs below the weight adjusted equivalent to the rat LD50 for subcutaneous caesium chloride injection. A series of columns (≤5) were used to buffer exchange each purification lot such that the specified volumes could be applied and collected. The virus peak was collected as a single fraction from each column and the fractions were pooled to generate a concentrated purification lot. From a QC virus particle determination, the lot was diluted with ice cold A438 to between $2-3\times10^{11}$ vp/mL and filtered through a 0.45 micron filter (Millipore Millex HV 33 mm diameter PVDF disc filter) to remove large virus aggregates. Each purification lot was snap frozen in isopropyl alcohol/dry ice and stored at −80° C. The maximum hold time was 1 hour post formulation.

The final dosage form is presented in glass vials of 0.6 mL. Each vial of AdCh63 ME.TRAP contains $1.3\times10^{11}$ vp/mL formulated in 10 mM Histidine, 7.5% sucrose, 35 mM NaCl, 1 mM MgCl$_2$, 0.1% PS80, 0.1 mM EDTA, 0.5% ethanol, pH 6.6. (This titre was determined by absorbance at 260 nm). The dose of AdCh63 ME.TRAP to be used is typically between $1\times10^8$ vp and $5\times10^{10}$ vp by intradermal administration. The volume administered may alter, corresponding to any updated concentration.

Example 2—Testing of AdCh63 ME.TRAP Vector

Materials and Methods
Immunization of Mice

Female BALB/c mice 6 to 8 week of age were purchased from the Biomedical Services Unit at the John Radcliffe Hospital, Oxford with all animals undertaken in accordance with the terms of the U.K. Home Office Animals Act Project License. Immunizations were performed intradermally, which has previously been shown to elicit better immunogenicity when compared to other routes e.g. sub-cutaneous, intramuscular [11]. Adenoviruses were administered at a dose of $1\times10^{10}$ viral particles (v.p.) for experiments involving a single prime and lower doses of $5\times10^9$ vp for prime-boost protocols. MVA was used at a dose of $1\times10^7$ pfu for boosting the T-cell responses. All vectors were resuspended in endotoxin-free PBS prior to immunization.

Immunization and Analysis of T-Cell Responses in Macaques

Rhesus macaques were immunized by two different routes, intramuscular injection in deltoid muscles (macaque id numbers: 0033, 1029, 2013 and 4073) and intradermal administration (id numbers: 0043, 2009 and 6015) of AdCh63 ME.TRAP at a dose of $5\times10^{10}$ v.p. All macaques were given a boost by intradermal immunisation 8 weeks later with MVA ME.TRAP at a dose of $2\times10^8$ pfu.

An ex-vivo IFNγ ELISpot was performed by stimulating the T cells with 4 peptide pools spanning the whole region of ME.TRAP. Total responses to TRAP were calculated by adding responses to individual pools and subtracting a background value of non-stimulated samples that only contained DMSO.

Viral Vectors

All viral vectors used in the experiments, AdCh63, AdC9 and MVA, express the transgene ME.TRAP that has been previously described [5, 12]. As described elsewhere herein, insert ME.TRAP is a hybrid transgene of 2398 bp encoding a protein of 789 amino acids. The ME string contains the BALB/c H-2Kd epitope Pb9 amongst a number of other B- and T-cell epitopes [13]. The simian adenoviral vector AdC9. (SAdV) was constructed and propagated as described previously [14].

Manufacture and vector production for AdCh63 ME.TRAP was carried out as described in Example 1. AdCh63 has been successfully produced in good titres using this protocol and a similar protocol may be used to product ME.TRAP vectors based on alternative simian adenoviral vector backbones.

Ex Vivo IFNγ ELISPOT

ACK-treated splenocytes or PBMCs were cultured for 18-20 hours on IPVH-membrane plates (Millipore) with the immunodominant H-2Kd-restricted epitope Pb9 (SYIP-SAEKI) at a final concentration of 1 µg/ml. ELISPOT was performed as previously described [15].

ELISA

IgG antibodies against the TRAP region were analyzed by ELISA as described previously [16]. For this experiment, serum was obtained from groups of at least 3 BALB/c mice after 4 weeks of immunization with adenovirus-MVA prime-boost regimes.

Parasite Challenge

*Plasmodium berghei* (ANKA strain clone 234) sporozoites (spz) were isolated from salivary glands of female *Anopheles stephensi* mosquitoes. Parasites were resuspended in RPMI-1640 medium with each mouse receiving a total of 1,000 spz via the i.v. route. Blood samples were taken on daily basis from day 5 to 20; smears were stained with Giemsa and screened for the presence of schizonts within the red blood cells. Survival was defined as complete absence of parasites in blood.

Statistical Analysis

Statistical significance of flow cytometry samples were analyzed with either a one or two-way ANOVA and a Bonferroni post-test. All statistic tests were performed using GraphPad Prism version 4.03 for Windows, GraphPad Software, San Diego Calif., USA, www.graphpad.com.

Results
Immunogenicity Upon a Single Prime of AdCh63ME.TRAP in Mice

Figure 2:
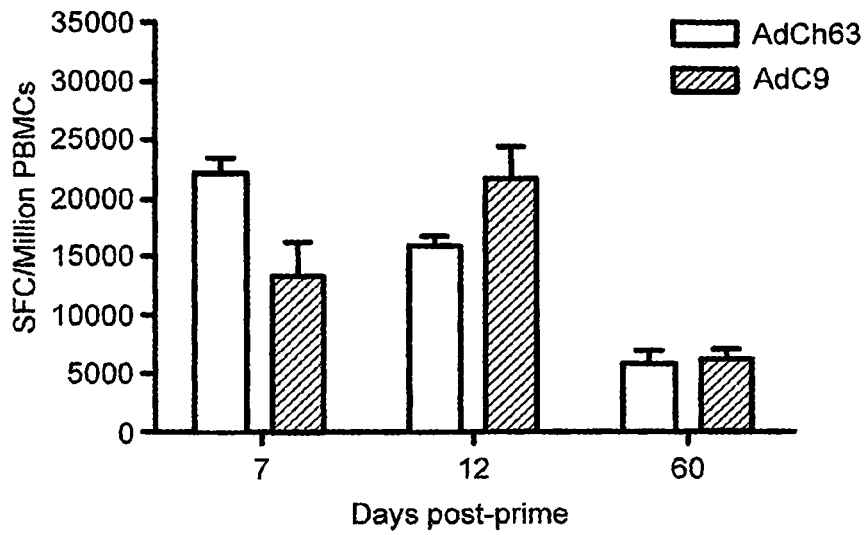
FIG. 2. Illustrates immunogenicity of AdCh63ME.TRAP after a single prime. 6-8 week-old BALB/c mice were immunized with $1\times10^{10}$ vp of simian adenoviral vectors AdCh63 and AdC9 coding for ME.TRAP. Immunogenicity was analyzed in blood by ELISpot on day 7, 12 and 60 post-immunization.

Upon a single immunization, adenoviral vectors were able to induce strong, long-term CD8+ T cell responses. FIG. 2 shows a comparison between AdCh63 and AdC9 both coding for the ME.TRAP transgene. The presence of the immunodominant H-2Kd-restricted epitope Pb9 (SYIP-SAEKI) in the ME string of the transgene allowed us to assess the potency of the immune response elicited by the viral vectors. Results in our lab have shown that AdC9 is one of the most immunogenic vectors and is able to induce CD8+ T-cell responses that outperform the human serotype AdH5. FIG. 2 shows that AdCh63ME.TRAP induces similar responses to AdC9 over a period of time of 60 days. AdCh63 CD8 responses were significantly higher than AdC9 early after 7 days of vaccination and no significant differences were found afterwards. An important goal of any viral-vectored vaccine is the possibility to induce strong memory CD8+ T-cell responses and in that aspect both vectors, AdC9 and AdCh63 ME.TRAP showed similar immunogenicity even after a long period of time of 60 days.

Protection to a Challenge with *Plasmodium berghei* in Mice

Figure 3A:
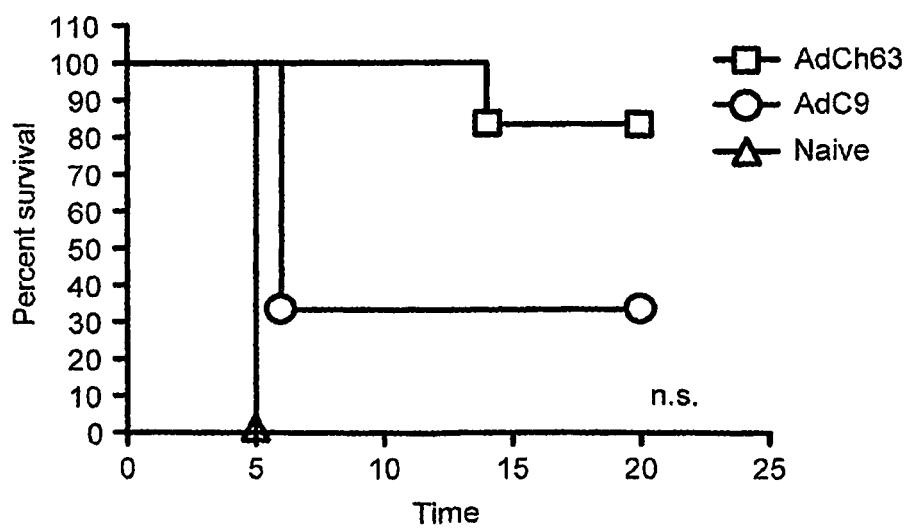
FIG. 3. Illustrates sterile protection and efficacy of simian adenoviral vectors AdCh63 and AdC9 coding for ME.TRAP to a parasite challenge. BALB/c mice were immunized with adenoviral ($1\times10^{10}$ vp) vectors and then challenged 14 days (n=6) and 60 days later (n=6) by i.v. administration of 1000 sporozoites of *Plasmodium berghei*.
Figure 3B:
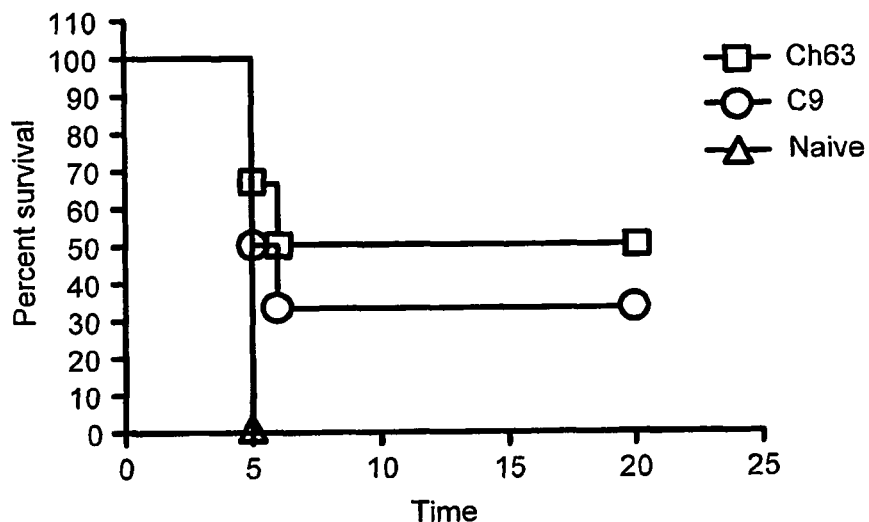

The results of this study have shown for the first time that a single vaccination with adenoviral vectors can elicit high levels of sterile protection to malaria upon a challenge with *P. berghei* sporozoites. Initial experiments have shown that vectors such as AdH5, AdC7 and AdC9 are able to protect a high percentage of mice after only one vaccination (at doses of $1 \times 10^{10}$ v.p). FIG. 3 shows a comparison of protective levels of AdCh63ME.TRAP with AdC9 shortly after immunization on day 14 (a) and after a long period of time of 60 days (b) between the vaccine administration and the challenge. Despite similar immunogenicity by both vectors over the time (FIG. 2), protective levels elicited by AdCh63 ME.TRAP outperformed AdC9 at both time points. Of particular importance, we found that upon a challenge at day 14 post-vaccination, AdCh63 protected all mice against infection for 15 days and at the end of the experiment only 1 mouse out of 6 was infected. AdC9 showed lower levels of protection on the short (FIG. 3a) and long (FIG. 3b) term.

Prime-Boost Regimes

Figure 4A:
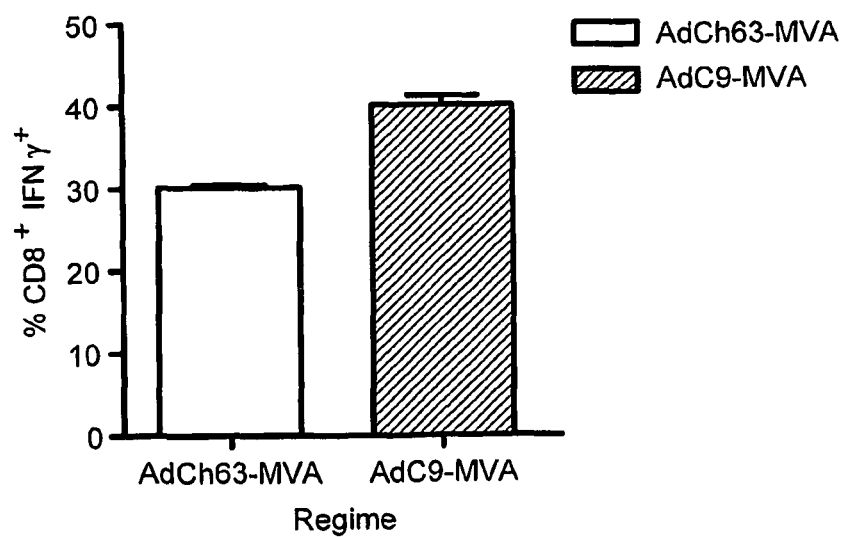
FIG. 4. Illustrates immunogenicity by adenovirus-MVA prime-boost regimes. BALB/c mice were vaccinated with ($5\times10^9$ vp) the simian adenoviral vectors AdCh63 and AdC9 coding for ME.TRAP. All mice were re-immunized 8 weeks later with MVA ME.TRAP (1×10⁷ pfu) and T cell responses were assessed by flow cytometry after 14 days (a) and by ELISpot on days 63 and 182 post-boost (b) d. Induction of IgG antibodies was also quantified by ELISA 28 days after the boost with MVA (c).
Figure 4B:
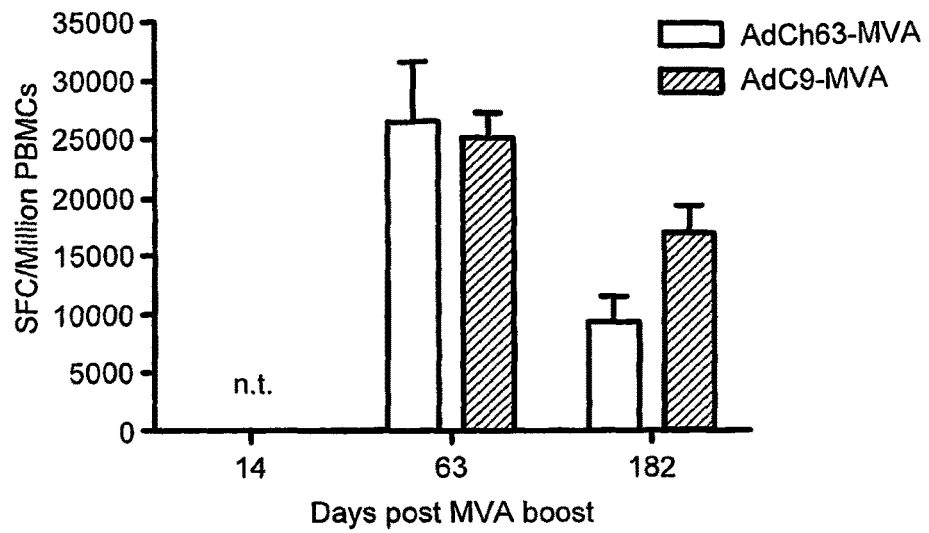
Figure 4C:
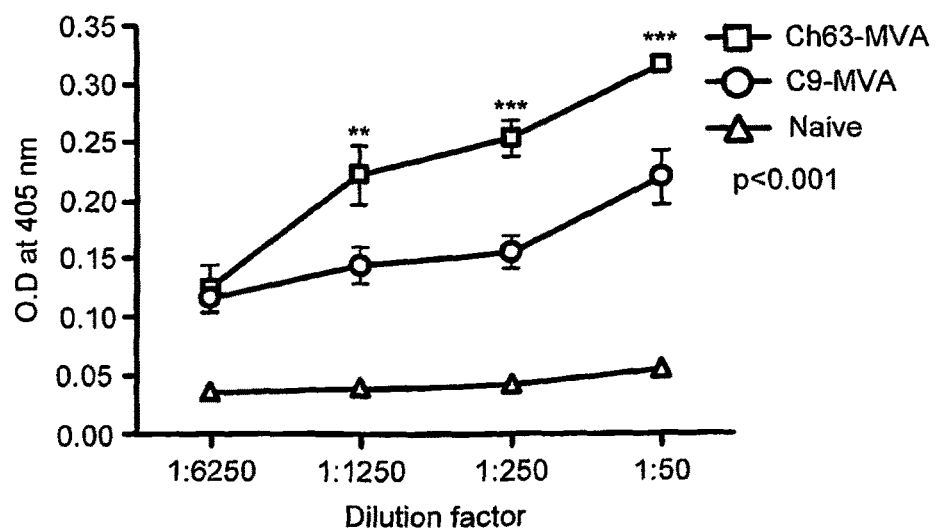

It has been reported that priming with AdH5 followed by a boost with MVA (A-M regimes) coding for the same transgene, increases immunogenicity when compared to a single administration of a vector or to prime-boost regimes with other vectors such as DNA or FP9 followed by MVA (11). We have therefore tested an approach using prime-boost regimes combining a simian adenoviral vector followed 8 weeks later by the poxviral vector MVA. FIG. 4 shows a comparison between CD8+ T-cell responses (FIG. 4a,b) and antibody responses (FIG. 4c) elicited by AdCh63-MVA and AdC9-MVA regimes. Shortly after immunization (FIG. 4a), AdCh63 showed high levels of CD8 responses, and although AdC9 responses were more potent, no statistical differences were found. Analysis of the responses on the long term showed the great advantage of a prime-boost regime over a single prime. As shown in FIG. 4b, the CD8 responses remained high even at day 60 post-boost (>25,000 SEC/million PBMCs) and contrasted with the levels at the same time point upon a single vaccination (<10,000 SEC/million PBMCs, FIG. 2). Six months after an MVA boost, the immunogenicity levels remained still above 10,000 spots/million PBMCs and no significant differences were found amongst the two simian adenoviral vectors tested.

Although protection efficacy relies on the cellular immune responses in this system, adenoviral vectors offer the additional advantage of inducing strong transgene-specific antibody responses [17]. This feature is potentially important when the adenoviral vectors are used for vaccine purposes in humans due to the extra protection that antibodies provide in addition to the cellular immune responses. Humoral responses were assessed by quantifying the IgG elicited by A-M prime-boost regimes. As shown in FIG. 4c, antibody responses were high for both regimes tested and the use of an AdCh63-MVA combination resulted in significantly higher IgG levels compared to AdC9.

Figure 5A:
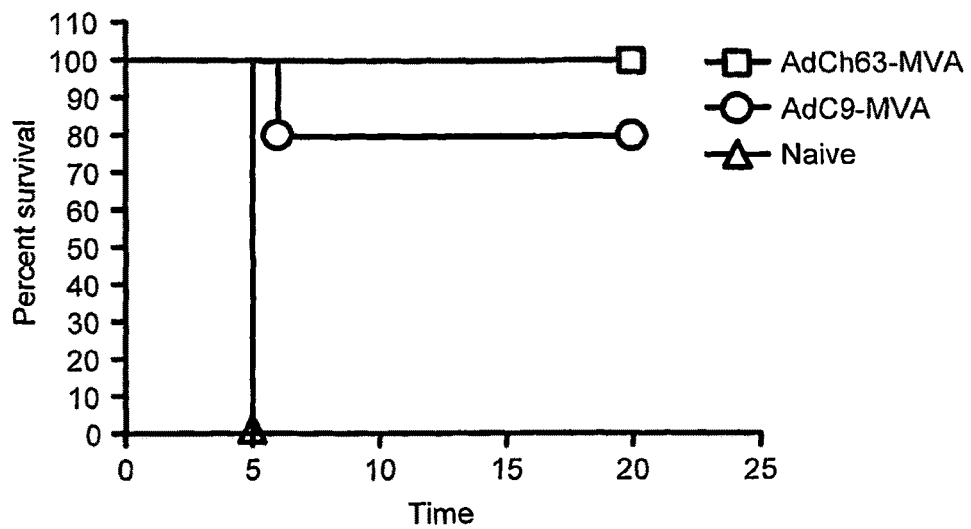
FIG. 5. Illustrates sterile protection and efficacy of adenoviral-MVA prime-boost regimes to a parasite challenge.
Figure 5B:
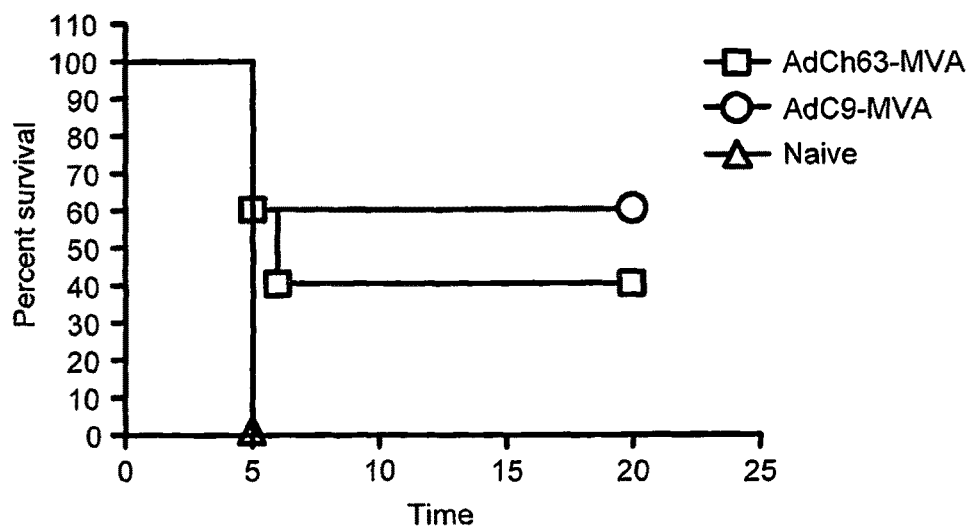
Figure 5C:
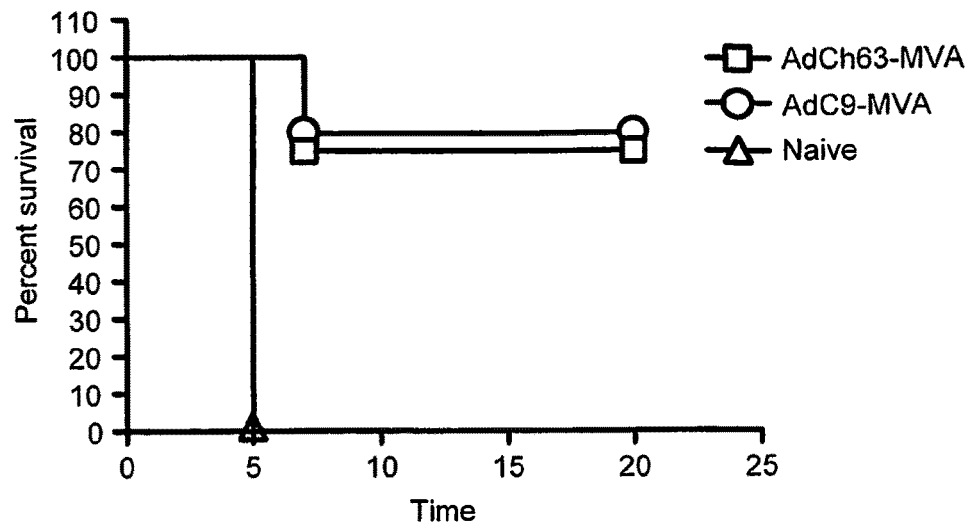

Since the immunogenicity levels were improved by prime-boost regimes, the levels of sterile protection were analyzed using the same strategy of sequential vaccination (FIG. 5). Outstanding levels were found at short and long intervals after the boost in both regimes. However, the AdCh63-MVA regime outperformed the AdC9-MVA at all time points tested. Of interest, the AdCh63-MVA regime elicited sterile protection in 100% of the animals on the short term. Despite the protection decreasing with the time, it remained high and strikingly both regimes induced outstanding levels of protection even six months after the boosting vaccination (FIG. 5c).

Immunogenicity in Rhesus Macaques

In many prior art examples, the efficacy of vectored vaccines is observed to decrease when tested in nonhuman primates or humans, as compared to responses in mice. Therefore, a prime-boost regime similar to the one described above in mice was tested in Rhesus macaques.

Seven rhesus macaques were immunised with a dose of $5 \times 10^{10}$ vp of AdCh63 ME.TRAP vaccine prepared according to example 1. The vaccine was administered either intradermally or intramuscularly, but as no difference in immunogenicity was observed between the routes the combined data are shown. At various times after immunisation with AdCh63 ME.TRAP booster immunisations with a heterologous viral vector, MVA encoding ME.TRAP, were administered (see FIG. 7). The data show (FIG. 8) that AdCh63 ME.TRAP was highly immunogenic in macaque monkeys, a species widely regarded as usefully predictive of vaccine immunogenicity in humans. After a single immunisation mean T cell responses were observed of about 1000 SFU per million PBMCs in ELISPOT assays, a level previously associated with protection in humans for this vaccine insert (Webster et al. PNAS 2005 102:4836-41). Also strong antibody titres with induced by vaccination. Heterologous booster immunisations with MVA could boost both the T cell and antibody responses to even higher levels. Limited analysis of the phenotype of T cells from selected time points showed that both CD8 and CD4 T cells were induced by the vaccination regimes and that these could be polyfunctional cells that express interferon-gamma, TNF and IL2.

Figure 6A:
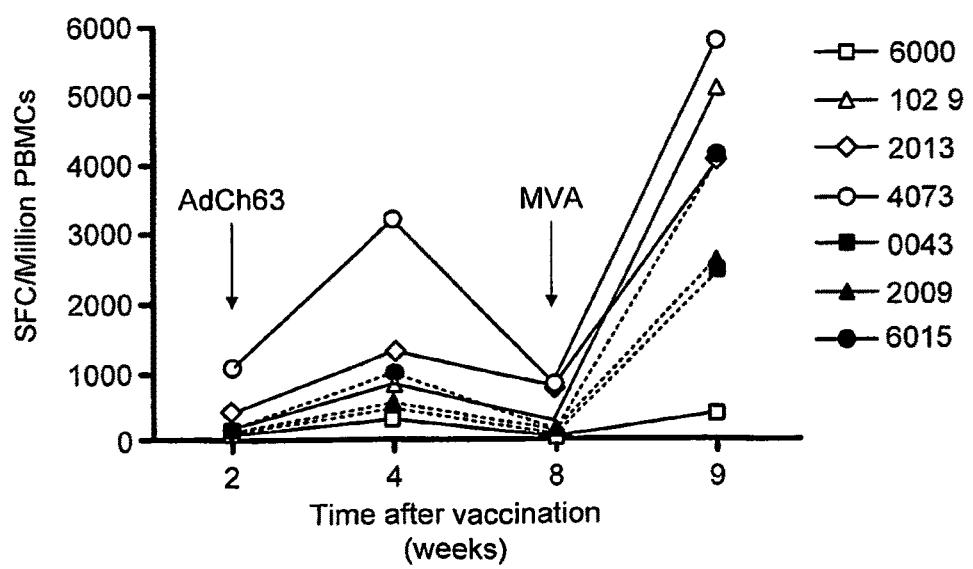
Figure 6B:
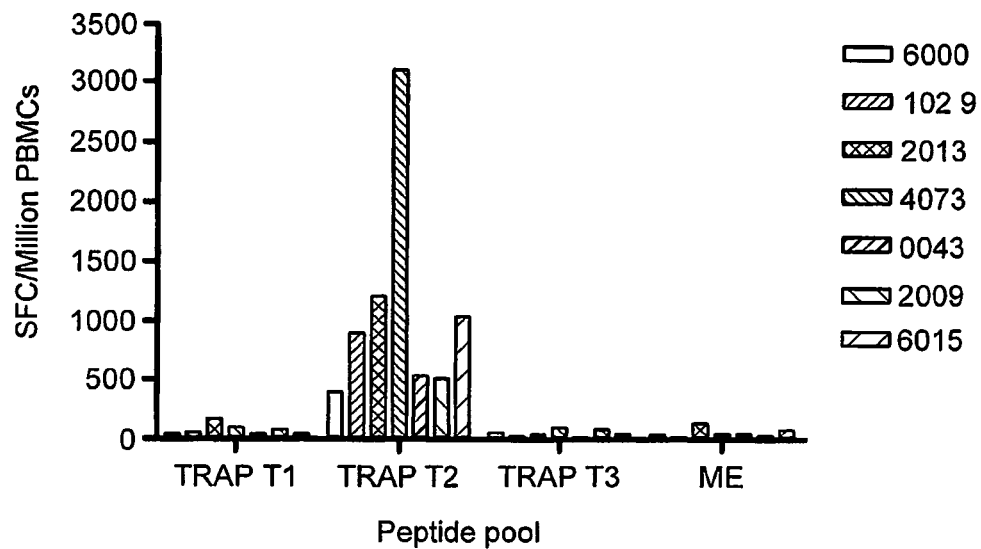
Figure 6C:
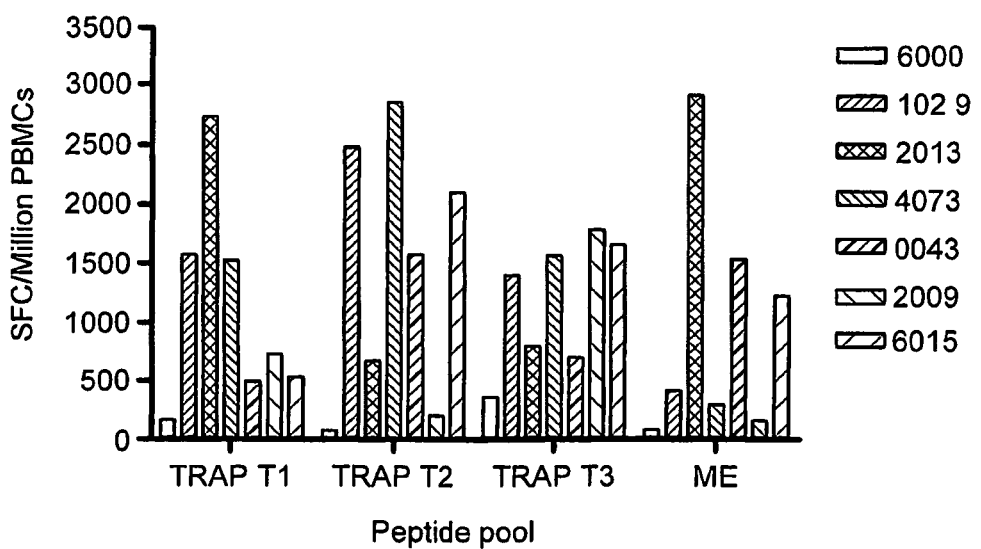

As shown in FIG. 6a, priming with AdCh63ME.TRAP elicited robust T-cell responses that peaked at week 4 after vaccination. Of interest, all macaques but one (4073) were juveniles that weighed between 3-4 kg, whereas the older and heavier animal no. 4073 (more than 10 kg) showed exceptionally good immune responses upon priming. Importantly, the T-cell responses could be boosted by a subsequent vaccination with MVA ME.TRAP and up to five-fold differences were found in some cases when comparing the peak of a prime versus the peak after a boost. Additional observations were made after comparing the immune responses to peptide pools that span the complete ME.TRAP region. The T-cell responses were mainly focused to the pool T2 after the AdCh63 prime (FIG. 6b). However, the MVA boost gave the additional advantage of an increased breadth in the immune response to ME.TRAP, where the main focus was not only T2 but also towards the complete ME.TRAP sequence (FIG. 6c). Importantly, these strong T cell responses induced in macaques are probably the strongest ever induced to a malaria antigen and are much higher than the T cell responses induced to ME.TRAP by any clinical trial undertaken to date. Because the magnitude of the T cell responses induced to TRAP has been correlated with the amount of protection measured in human clinical trials (Webster et al. PNAS; Dunachie et al Infection and Immunity) we anticipate that this vaccine regime should be more effective than any ME.TRAP vaccine tested to date in humans.

Use of AdCh63 ME.TRAP in Humans

The simian adenoviral vector AdCh63 ME.TRAP has been evaluated in a phase I human clinical trial to test safety and immunogenicity in humans by a single immunization of AdCh63 ME.TRAP and a prime-boost regime involving the previous adenovirus followed by an MVA boost 8 weeks later.

All volunteers recruited were healthy male adults. As this was the first time a chimpanzee adenovirus vector had been assessed in humans the first group of vaccinees received a very low dose of vaccine, $10^8$ vp. This may be contrasted with the $5 \times 10^{10}$ vp dose administered to macaques and $1-10 \times 10^{10}$ vp was used a typical dose in previous vaccine trials of human adenovirus vectors. At this low dose of $10^8$ vp both local and systemic safety in the first eight volunteers was excellent. Four of these individuals received a booster immunisation with MVA encoding ME.TRAP at a dose of $2 \times 10^8$ pfu. The time course of T cell immunogenicity in these four volunteers is shown, as an average response in FIG. 9. Immunogenicity was measured by ex vivo gamma-interferon ELISPOT to 15 mer peptide pools overlapping the vaccine insert: T9/96 TRAP 15 mer, and also to the same sequence with overlapping 20mer peptides: T9/96 TRAP 20mer. Also shown is the response to 20mer peptides representing a heterologous strain of P. falciparum: 3D7 TRAP 20mer. Finally, the response to the short string of mainly nonamer malaria peptide epitopes in the ME-polyepitope string (Gilbert et al. Nature Biotechnol. 1997 November; 15:1280-4) is shown: ME.

These results show that even at the very low dosage used detectable T cell responses to TRAP are observed at four weeks after a single immunisation with AdCh63 ME.TRAP in humans. Additionally these responses can be strongly boosted by the MVA vaccine indicating that memory T cells are primed in humans by the adenoviral vector.

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

REFERENCES

1 Snow, R. W., Guerra, C. A., Noor, A. M., Myint, H. Y. and Hay, S. I., The global distribution of clinical episodes of Plasmodium falciparum malaria. Nature 2005. 434: 214-217.

2 Hill, A. V., Pre-erythrocytic malaria vaccines: towards greater efficacy. Nat Rev Immunol 2006. 6: 21-32.

3 Tsuji, M. and Zavala, F., T cells as mediators of protective immunity against liver stages of Plasmodium. Trends Parasitol 2003. 19: 88-93.

4 Khusmith, S., Charoenvit, Y., Kumar, S., Sedegah, M., Beaudoin, R. L. and Hoffman, S. L., Protection against malaria by vaccination with sporozoite surface protein 2 plus CS protein. Science 1991. 252: 715-718.

5 Gilbert, S. C., Plebanski, M., Harris, S. J., Allsopp, C. E., Thomas, R., Layton, G. T. and Hill, A. V., A protein particle vaccine containing multiple malaria epitopes. Nat Biotechnol 1997. 15: 1280-1284.

6 Moorthy, V. S., McConkey, S., Roberts, M., Gothard, P., Arulanantham, N., Degano, P., Schneider, J., Hannan, C., Roy, M., Gilbert, S. C., Peto, T. E. and Hill, A. V., Safety of DNA and modified vaccinia virus Ankara vaccines against liver-stage P. falciparum malaria in non-immune volunteers. Vaccine 2003. 21: 1995-2002.

7 Rodrigues, E. G., Zavala, F., Eichinger, D., Wilson, J. M. and Tsuji, M., Single immunizing dose of recombinant adenovirus efficiently induces CD8+ T cell-mediated protective immunity against malaria. J Immunol 1997. 158: 1268-1274.

8 Zhi, Y., Figueredo, J., Kobinger, G. P., Hagan, H., Calcedo, R., Miller, J. R., Gao, G. and Wilson, J. M., Efficacy of Severe Acute Respiratory Syndrome Vaccine Based on a Nonhuman Primate Adenovirus in the Presence of Immunity Against Human Adenovirus. Hum Gene Ther 2006.

9 Fitzgerald, J. C., Gao, G. P., Reyes-Sandoval, A., Pavlakis, G. N., Xiang, Z. Q., Wlazlo, A. P., Giles-Davis, W., Wilson, J. M. and Ertl, H. C., A simian replication-defective adenoviral recombinant vaccine to HIV-1 gag. J Immunol 2003. 170: 1416-1422.

10 Reyes-Sandoval, A., Fitzgerald, J. C., Grant, R., Roy, S., Xiang, Z. Q., Li, Y., Gao, G. P., Wilson, J. M. and Ertl, H. C., Human immunodeficiency virus type 1-specific immune responses in primates upon sequential immunization with adenoviral vaccine carriers of human and simian serotypes. J Virol 2004. 78: 7392-7399.

11 Gilbert, S. C., Schneider, J., Hannan, C. M., Hu, J. T., Plebanski, M., Sinden, R. and Hill, A. V., Enhanced CD8 T cell immunogenicity and protective efficacy in a mouse malaria model using a recombinant adenoviral vaccine in heterologous prime-boost immunisation regimes. Vaccine 2002. 20: 1039-1045.

12 McConkey, S. J., Reece, W. H., Moorthy, V. S., Webster, D., Dunachie, S., Butcher, G., Vuola, J. M., Blanchard, T. J., Gothard, P., Watkins, K., Hannan, C. M., Everaere, S., Brown, K., Kester, K. E., Cummings, J., Williams, J., Heppner, D. G., Pathan, A., Flanagan, K., Arulanantham, N., Roberts, M. T., Roy, M., Smith, G. L., Schneider, J., Peto, T., Sinden, R. E., Gilbert, S. C. and Hill, A. V., Enhanced T-cell immunogenicity of plasmid DNA vaccines boosted by recombinant modified vaccinia virus Ankara in humans. Nat Med 2003. 9: 729-735.

13 Schneider, J., Gilbert, S. C., Blanchard, T. J., Hanke, T., Robson, K. J., Hannan, C. M., Becker, M., Sinden, R., Smith, G. L. and Hill, A. V., Enhanced immunogenicity for CD8+ T cell induction and complete protective efficacy of malaria DNA vaccination by boosting with modified vaccinia virus Ankara. Nat Med 1998. 4: 397-402.

14 Roy, S., Gao, G., Lu, Y., Zhou, X., Lock, M., Calcedo, R. and Wilson, J. M., Characterization of a family of chimpanzee adenoviruses and development of molecular clones for gene transfer vectors. Hum Gene Ther 2004. 15: 519-530.

15 Moore, A. C., Gallimore, A., Draper, S. J., Watkins, K. R., Gilbert, S. C. and Hill, A. V., Anti-CD25 antibody enhancement of vaccine-induced immunogenicity: increased durable cellular immunity with reduced immunodominance. J Immunol 2005. 175: 7264-7273.

16 Webster, D. P., Dunachie, S., Vuola, J. M., Berthoud, T., Keating, S., Laidlaw, S. M., McConkey, S. J., Poulton, I., Andrews, L., Andersen, R. F., Bejon, P., Butcher, G., Sinden, R., Skinner, M. A., Gilbert, S. C. and Hill, A. V., Enhanced T cell-mediated protection against malaria in human challenges by using the recombinant poxviruses FP9 and modified vaccinia virus Ankara. *Proc Natl Acad Sci USA* 2005. 102: 4836-4841.

17 Xiang, Z., Gao, G., Reyes-Sandoval, A., Cohen, C. J., Li, Y., Bergelson, J. M., Wilson, J. M. and Ertl, H. C., Novel, chimpanzee serotype 68-based adenoviral vaccine carrier for induction of antibodies to a transgene product. *J Virol* 2002. 76: 2667-2675.

18 Sacre, K., Carcelain, G., Cassoux, N., Fillet, A. M., Costagliola, D., Vittecoq, D., Salmon, D., Amoura, Z., Katlama, C. and Autran, B., Repertoire, diversity, and differentiation of specific CD8 T cells are associated with immune protection against human cytomegalovirus disease. *J Exp Med* 2005. 201: 1999-2010.

The invention claimed is:

1. A recombinant replication defective simian adenovirus vector capable of eliciting a protective response to *Plasmodium berghei* challenge in mice, comprising a nucleotide sequence encoding a multiple epitope thrombospondin-related adhesion (ME.TRAP) protein comprising SEQ ID NO:2, said nucleotide sequence operably linked to regulatory sequences which direct expression of said ME.TRAP protein in mammalian cells, wherein the simian adenoviral vector is replication defective chimpanzee adenovirus isolate 63 (AdCh63).

2. The recombinant replication defective simian adenovirus vector of claim 1 wherein the regulatory sequences which direct expression of said ME.TRAP protein comprise a CMV promoter.

3. The recombinant replication defective simian adenovirus vector of claim 2 wherein the regulatory sequences comprise the promoter of the HCMV IE1 gene and a fragment of the 5' untranslated region of the HCMV IE1 gene including intron A.

4. An immunogenic composition comprising the recombinant replication defective simian adenovirus vector of claim 1 admixed with one or more pharmaceutically acceptable vehicles, carriers, diluents or adjuvants.

5. A method of eliciting an immune response against ME.TRAP protein comprising SEQ ID NO:2 in a human subject, which comprises administering to the subject an amount of the immunogenic composition of claim 4 which is sufficient to elicit said immune response in said subject.

6. The method of claim 5 wherein the immunogenic composition is administered in an amount sufficient to elicit a T-cell-mediated response against ME.TRAP protein comprising SEQ ID NO:2.

7. The method of claim 5 wherein the immunogenic composition is administered as a single dose immunization.

* * * * *